US009186191B2

(12) United States Patent
Berrevoets et al.

(10) Patent No.: US 9,186,191 B2
(45) Date of Patent: Nov. 17, 2015

(54) ROD COUPLING ASSEMBLY AND METHODS FOR BONE FIXATION

(71) Applicant: PIONEER SURGICAL TECHNOLOGY, INC., Marquette, MI (US)

(72) Inventors: Gregory Berrevoets, Skandia, MI (US); Scott J. Perrow, Ishpeming, MI (US)

(73) Assignee: PIONEER SURGICAL TECHNOLOGY, INC., Marquette, MI (US)

( * ) Notice: Subject to any disclaimer, the term of this patent is extended or adjusted under 35 U.S.C. 154(b) by 391 days.

(21) Appl. No.: 13/846,562

(22) Filed: Mar. 18, 2013

(65) Prior Publication Data

US 2013/0345756 A1    Dec. 26, 2013

Related U.S. Application Data

(63) Continuation of application No. 12/257,285, filed on Oct. 23, 2008, now Pat. No. 8,398,683.

(60) Provisional application No. 60/981,821, filed on Oct. 23, 2007.

(51) Int. Cl.
*A61B 17/88* (2006.01)
*A61B 17/70* (2006.01)

(52) U.S. Cl.
CPC ............... *A61B 17/88* (2013.01); *A61B 17/70* (2013.01); *A61B 17/7001* (2013.01); *A61B 17/7032* (2013.01); *A61B 17/7035* (2013.01); *A61B 17/7037* (2013.01); *A61B 17/7049* (2013.01)

(58) Field of Classification Search
CPC ............... A61B 17/70; A61B 17/7001; A61B 17/7032; A61B 17/7035; A61B 17/7037; A61B 17/88
USPC ............... 606/246–247, 264–274, 300–301, 606/304–308, 319
See application file for complete search history.

(56) References Cited

U.S. PATENT DOCUMENTS

| | | | | |
|---|---|---|---|---|
| 5,672,176 A | * | 9/1997 | Biedermann et al. | 606/271 |
| 6,355,040 B1 | * | 3/2002 | Richelsoph et al. | 606/272 |
| 2007/0225711 A1 | * | 9/2007 | Ensign | 606/61 |

* cited by examiner

*Primary Examiner* — Larry E Waggle, Jr.
(74) *Attorney, Agent, or Firm* — Fitch, Even, Tabin & Flannery LLP

(57) ABSTRACT

A coupling device for securing an elongate member to the spine is provided. The coupling device comprises a compressible inner member that secures an anchor member therein when the inner member is axially shifted within an outer member. Structures are provided to prevent disassembly of the anchor and coupling device prior to locking of the elongate member.

16 Claims, 18 Drawing Sheets

ROD COUPLING ASSEMBLY AND METHODS FOR BONE FIXATION

CROSS-REFERENCED TO RELATED APPLICATIONS

This application is a continuation of prior U.S. application Ser. No. 12/257,285, filed Oct. 23, 2008, which claims the benefit of U.S. Provisional Application 60/981,821, filed Oct. 23, 2007, which are fully incorporated by reference as if reproduced in their entirety herein.

FIELD OF THE INVENTION

The present systems and methods provide for a low profile coupling assembly configured to secure an elongate member or rod to vertebrae. In particular, coupling assemblies having different degrees of locking are provided for receiving and retaining an anchor member and rod, and then fully locking the anchor member and rod against movement relative to the assembly.

BACKGROUND OF THE INVENTION

Various devices for internal fixation of bone segments in the human or animal body are known in the art. For instance, pedicle screw and/or hook systems are sometimes used as an adjunct to spinal fusion surgery, and which provides a means of gripping a spinal segment. Such systems may have a rod-receiving portion and an integral anchor portion, or may be provided with a separate anchor member, especially one that may be pivoted with respect to a rod-receiving member. Although pedicle screw systems, comprising a pedicle screw and a rod-receiving device, are primarily discussed herein, it is also possible to anchor a rod-receiving device to the spine with a different type of anchor member, such as a laminar hook. The pedicle screw of such a system includes an externally threaded stem and a head portion. The rod-receiving device (also referred to as a coupling device) couples to the head portion of the pedicle screw and receives a spinal rod. Two or more such devices are inserted into respective vertebrae and adjusted along the spinal rod to distract, de-rotate, and/or stabilize a spinal column, for instance to correct scoliosis or stabilize the spinal column in conjunction with an operation to correct a herniated disk. The pedicle screw does not, by itself, fix the spinal segment, but instead operates as an anchor point to receive the rod-receiving device, which in turn receives the rod. One goal of such a system is to substantially reduce and/or prevent relative motion between the spinal segments that are being fused.

Pedicle screw systems may be configured for minimally invasive surgery (MIS) techniques. MIS techniques require implantation, manipulation, and locking of the pedicle screw system through a very small incision in the patient's skin. It has been suggested that one possible advantage of a MIS approach is that it can decrease a patient's recovery time.

Conventional pedicle screw systems and even more recently designed pedicle screw systems have several drawbacks. Some pedicle screw systems include rather large and bulky assemblies to secure a rod, thus increasing opportunities for tissue damage in and around the surgical site during installation. Many of these systems also include set-screw type locking mechanisms or multi-part cap structures that require a significant portion of the assembly to be located above the rod, increasing the height or profile of the implants extending radially away from the spinal column, which may cause patient discomfort after implantation. Systems with set screws also lack a predetermined locking position, often resulting in overtorquing of the locking mechanism. Many systems also require a rod-receiving device to be coupled to the pedicle screw or other anchor device prior to implantation or include numerous components that must all be carefully assembled together, making these systems more difficult to install and maneuver in a spinal operation where MIS techniques are used.

Furthermore, assemblies with polyaxial fixation devices in the prior art ordinarily rely on downward force of the rod against the head of the fixation device to secure the fixation device against pivoting, so that the assembly, and specifically the rod receiving portion thereof, is provided with little support or stability prior to full locking of the rod.

SUMMARY OF THE INVENTION

Low profile coupling devices for coupling an elongate member, such as a spinal rod, to one or more anchor members attached to vertebrae are provided herein. In order to ensure that the coupling assembly remains coupled to the anchor member during manipulation to receive and capture a spinal rod, structures and methods are provided for provisionally locking the anchor to the coupling assembly. When provisionally locked, the anchor may be pivoted with respect to the coupling assembly, but is held with sufficient force to remain coupled thereto under a significant load.

The rod-receiving or coupling assemblies include an outer member, an insert member for being received in the outer member, and a rod retaining member for securing the rod within the insert and/or outer members. The anchor member may include a screw, hook, or other bone fixation device for securing implants to bone. Although the anchor member may be formed integrally with the inner or outer member, it is preferably provided as a separate structure and more preferably pivotably received in the inner and/or outer member to allow the rod receiving device to be fixed at various angles with respect to the anchor. The outer member has an open space in its interior, and the insert member is linearly received in the space of the outer member. If the anchor member is received in the inner member, the inner member includes at least one flexible portion that is shifted against the anchor member during linear shifting of the insert member relative to the outer member. A linearly inserted rod retaining member interacts with the insert and/or outer members to shift a portion of the inner member against the elongate member, fixing the elongate member with respect to the coupling device. The assembly may be configured for independent locking of the anchor member and elongate member, so that one may be secured to the assembly before the other. For instance, the anchor member may be received within a lower portion of the insert member and secured therein by linear shifting of the insert member relative to the outer member, while the elongate member is received in an upper seat portion of the insert member and secured by linearly inserting the rod retaining member into engagement with the upper portion of the insert member. Improvements are provided that assist in retaining the anchor member prior to receipt and/or locking of the rod.

An exemplary coupling device configured to be coupled to couple a spinal rod to the head of a bone fixation device includes a generally cylindrical insert the inner member axially received in an interior space of an annular outer member to form a tulip-shaped assembly, such as the devices disclosed in 2007/0225711, which is hereby fully incorporated by reference herein. Other devices have also been disclosed that lock an anchor member in place through axial shifting of components. In one form, an insert member includes a lower portion with a generally spherical cavity configured to receive the head of an anchor member and an upper portion having a rod-receiving channel or seat. According to one exemplary embodiment, flexible, upstanding, laterally-spaced arms are arranged on either side of the channel and are configured to provisionally couple an elongate member by resiliently deflecting to grip a rod placed in the channel. The exemplary coupling assembly also includes an outer member or body having a bore, with at least a portion of the bore sized and configured to compress the insert member. After the head of the anchor member is received in the lower portion of the insert member, the outer member may be moved over the outer surface of the insert member, compressing the insert member to compressibly lock its lower portion onto the bone fixation device. A rod retaining device, such as a cap, locks the rod in place. For instance, the rod retaining device may be configured for linear insertion to engage the insert member and apply a compressive force radially toward the rod to secure the position of the rod. Such a rod retaining device may be provided in the form of a cap with at least one depending leg configured for friction fitting between the insert member and the outer member. Projections from the cap may be wedged between an upper portion of the insert member and the outer member, deflecting one or more flexible portions of the insert member toward the rod and applying a compressive locking force thereto. This locking force is transverse to the axis of the anchor member and the axis of the coupling assembly, so that little or no cap structure need be provided above the rod, thus minimizing the height of the assembly. While the cap or other rod lock member may be configured for linear insertion between the insert and outer member, it may also be configured to lock a rod by rotating into place or otherwise interacting with the insert and/or outer member to secure the rod in position. For instance, the cap may be in the form of a threaded member that threads onto the outer member or the insert, or a bayonet connector with flanges or slots configured to engage corresponding flanges or slots of the outer member or insert.

In one form, the insert member may have a lower annular wall that forms a cavity or orifice configured for pivotably receiving the head of the bone fixation device therein, and one or more axial slits or gaps that extend through the annular wall to provide the annular wall with flexibility, allowing for expansion of the cavity. In such an arrangement, the anchor member may be snap-locked into the cavity of the insert member by deflecting portions of the annular wall to temporarily widen the opening to the interior cavity. Preferably, the snap-lock fit may apply a light compressive force onto the head of the anchor member so that the insert member may be positioned about the anchor head and then released with the frictional force between the wall lower surface and the anchor head being sufficient to retain the insert member at a desired orientation relative to the anchor member. However, the snap-lock fit may instead loosely retain the head without significant friction. The head may also be loosely received in the insert member without snap-locking.

The outer member is configured to apply force onto the insert member, locking the anchor in place within the insert member. The outer member may have an interior space in the form of a through opening in which the insert member is received. In one form, the opening through the outer member may comprise at least one radially narrow portion and at least one radially wide portion, with the wide portion sized and configured to allow expansion of the insert member when located therein, and the narrow portion sized and configured to exert a radial compressive force upon the insert member. In such an embodiment, the head of the anchor member may be received by the insert member via a snap-lock fit therebetween when the insert member is located within the wide portion of the outer in a substantially non-compressed orientation. Alternatively, substantially the entire space may be sized so that the walls exert a radial compressive force upon the insert member inserted therein, or one or more protrusions in the space may be configured to compress the insert member.

Advantageously, the coupling assembly may be secured to the anchor member after the anchor is secured to the spine, substantially eliminating the need for invasive instruments designed to hold the assembly to the anchor member during implantation and allowing the anchor member to be positioned and secured to the spine without obstruction from the tulip assembly. The coupling assembly may then be provisionally coupled to the anchor member and pivoted to a desired angle before receiving the elongate member. The assembly may also be locked with respect to the anchor member in a fixed orientation relative thereto prior to receipt of the elongate member. Alternatively, the elongate member may be received in the inner tulip member prior to locking of the coupling assembly with respect to the fixation device.

The insert member and/or outer member may include one or more protrusions, recesses, or other structures to substantially keep the insert member from backing out of the inner space of the outer member once inserted in order to avoid disengagement of the anchor member from the insert member while the assembly is manipulated, for instance to receive the elongate member. The head of the anchor member may also be configured so that it may be shifted to multiple orientations within the insert member, at least one orientation reducing forces that expand the lower portion of the insert member in order to more securely retain the head within the tulip assembly.

BRIEF DESCRIPTION OF THE DRAWINGS

The accompanying drawings illustrate various exemplary embodiments of the present system and method, and do not limit the scope thereof.

Throughout the drawings, identical reference numbers designate similar but not necessarily identical elements.

DETAILED DESCRIPTION

Figure 1:
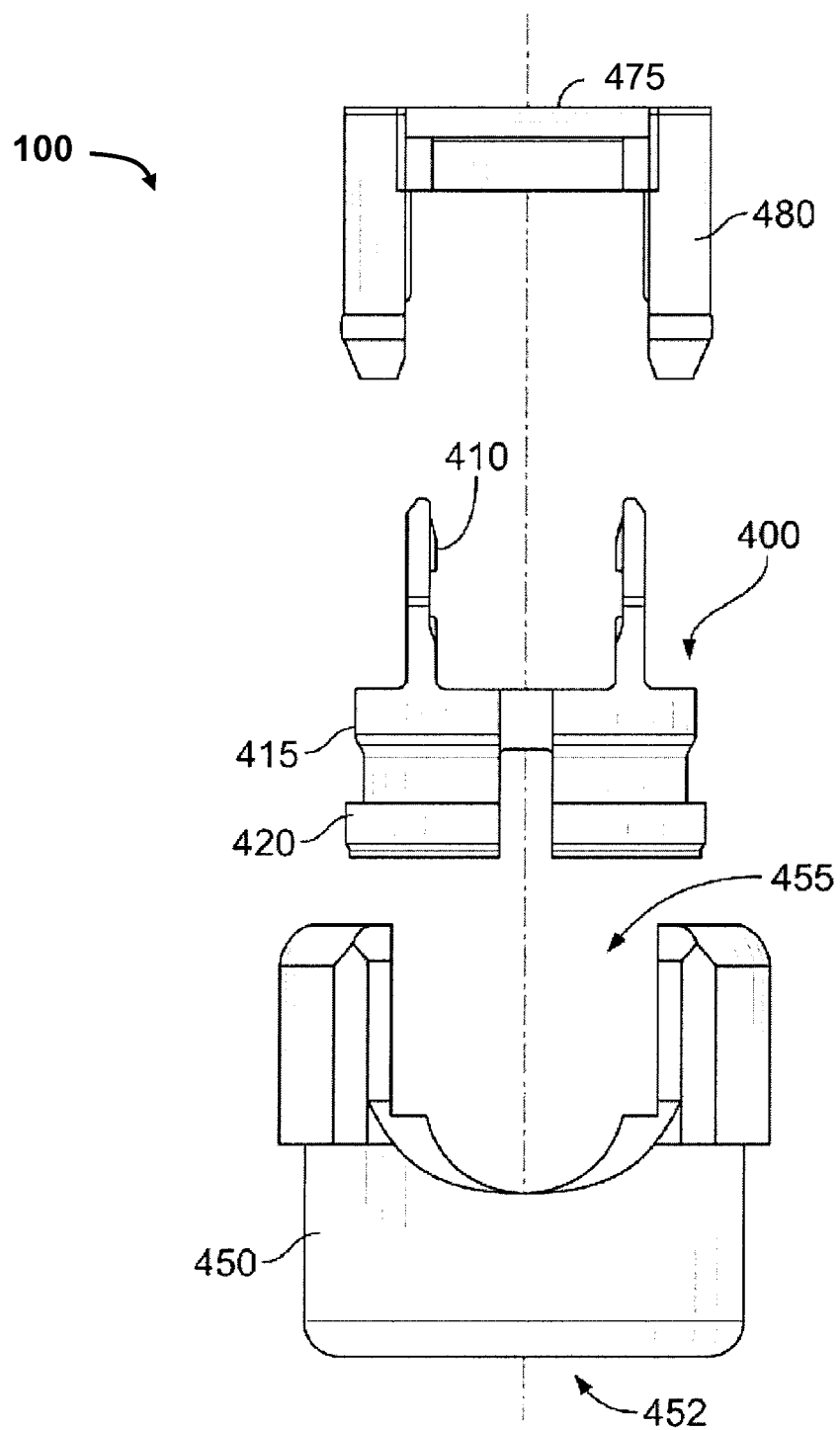
FIG. 1 is a front exploded view of a coupling assembly with components that are shifted linearly to lock an anchor member and spinal rod.

The present specification describes a system and a method for provisionally and fully locking the orientation of a coupling assembly (preferably a "tulip assembly" in which an insert member is inserted linearly into a space within an outer member) relative to an anchor member or fixation device (e.g. a pedicle screw or hook) and locking the assembly to an elongate member (e.g. a spinal rod) positioned along the spine. Locking may be accomplished by linear or axial movement of the components of the assembly, and may provide for separate locking of the fixation device and rod. Further, according to one exemplary embodiment, the present specification describes the structure of a coupling assembly configured to be placed on the head of a polyaxial pedicle screw after placement of the pedicle screw in a patient's body and configured to receive and positionally secure a top loaded rod. Further details of the present exemplary system and method will be provided below.

By way of example, pedicle screw systems may be fixed in the spine in a posterior lumbar fusion process via minimally invasive surgery (MIS) techniques. The systems are inserted into the pedicles of the spine and then interconnected with rods to manipulate (e.g., correct the curvature, compress or expand, and/or structurally reinforce) at least portions of the spine. Using the MIS approach to spinal fixation and/or correction surgery, in which implantation and manipulation of the system are accomplished through relatively small openings, has been shown to decrease a patient's recovery time and reduce the risks of follow-up surgeries.

The ability to efficiently perform spinal fixation and/or correction surgeries using MIS techniques is enhanced by the use of pedicle screw systems provided in accordance with the present exemplary systems and methods, which systems and methods provide a number of advantages over conventional systems. For example, a pedicle screw system in accordance with one embodiment of the present exemplary system and method provides the advantage that the pedicle screw (or other type of anchor member) may be inserted into the bone without being pre-operatively coupled with the coupling assembly. This is advantageous because the surgeon often needs to do other inter-body work after inserting the pedicle screw, but before attaching the larger and bulkier coupling assembly. This also allows the fixation device to be positioned within the body and secured to the spine without the assembly obscuring the surgeon's view or contact with the pedicle screw. Such an advantageous pedicle screw system may be even more crucial when using MIS techniques because the inter-body spatial boundaries in which the surgeon must work may be quite limited.

In addition, pedicle screw systems in accordance with the present systems and methods may advantageously allow a user to fix (e.g., lock) the coupling assembly to the pedicle screw at a desired angle either before or after inserting and/or capturing the rod. Fixing or locking the coupling assembly to the pedicle screw means that at least one of the components of the coupling assembly is manipulated to grip and/or clamp onto the pedicle screw to reduce and/or prevent any translational and/or rotational movement of the coupling assembly relative to the pedicle screw. In fact, the assembly may be configured to have both provisional screw lock and final screw lock positions, so that in the provisional screw lock position or positions the coupling assembly grips the screw head with sufficient force to retain the screw and/or maintain a selected angulation of the assembly with respect to the screw unless force is applied by hand or instrument to change said angulation, whereas the final screw lock position applies a greater force to the screw head than the provisional lock and maintains the assembly at a selected angulation with respect to the screw with sufficient force to prevent movement thereof under physiological loads generated by the body. The ability to provisionally and fully lock the coupling assembly to the pedicle screw prior to placing the rod into the coupling assembly may facilitate the surgeon in performing compression and/or distraction of various spinal and/or bone sections.

Similarly, the assembly may have provisional rod locking positions for loosely retaining the rod so that it is coupled to the assembly but may still be manipulated (e.g. shifted or rotated) therein prior to full rod locking.

The term "distraction," when used herein and when used in a medical sense, generally relates to joint surfaces and suggests that the joint surfaces move perpendicular to one another. However when "traction" and/or "distraction" is performed, for example on spinal sections, the spinal sections may move relative to one another through a combination of distraction and gliding, and/or other degrees of freedom.

The complete coupling assembly can be coupled to the head portion of the pedicle screw intra-operatively. The coupling assembly may include aspects or features that enable the coupling assembly to be provisionally or fully locked onto the head portion of the pedicle screw and then to further receive, capture, and finally lock the rod into the coupling assembly. A provisional lock configuration allows the coupling assembly to be secured to the anchor member without fully locking either the anchor or rod. Advantageously, the provisional lock prevents de-coupling of the assembly and anchor when the assembly is pulled, pivoted, or otherwise manipulated or placed under stress in order to position a spinal rod therein. The coupling assembly also may be coupled to the pedicle screw, and even provisionally and/or finally locked to the screw, prior to implantation of the screw into bone so that the screw and coupling assembly are implanted simultaneously. Furthermore, the screw locking and rod locking steps may be accomplished simultaneously rather than as separate steps. In addition to accommodating the MIS approach to spinal correction and/or fusion, the present exemplary systems and methods are configured to eliminate instances of cross-threading and/or post-operative splaying of the assembly, which may be caused by forces exerted by postoperative back flexion that open the coupling assembly and eventually lead to the disassembly and/or the failure of the pedicle screw system.

In the following description, for purposes of explanation, numerous specific details are set forth in order to provide a thorough understanding of the present system and method for providing a low top pedicle screw coupling system that is capable of separately locking the orientation of a coupling assembly relative to a pedicle screw and a positional location of a rod in the coupling assembly. It will be apparent, however, to one skilled in the art that the present method may be practiced without these specific details. Reference in the specification to "one embodiment" or "an embodiment"

means that a particular feature, structure, or characteristic described in connection with the embodiment is included in at least one embodiment. The appearance of the phrase "in one embodiment" in various places in the specification are not necessarily all referring to the same embodiment.

While the present systems and methods may be practiced by or incorporated into any number of bone fixation systems, the present systems and methods will be described herein, for ease of explanation only, in the context of a pedicle screw system.

Figure 2:
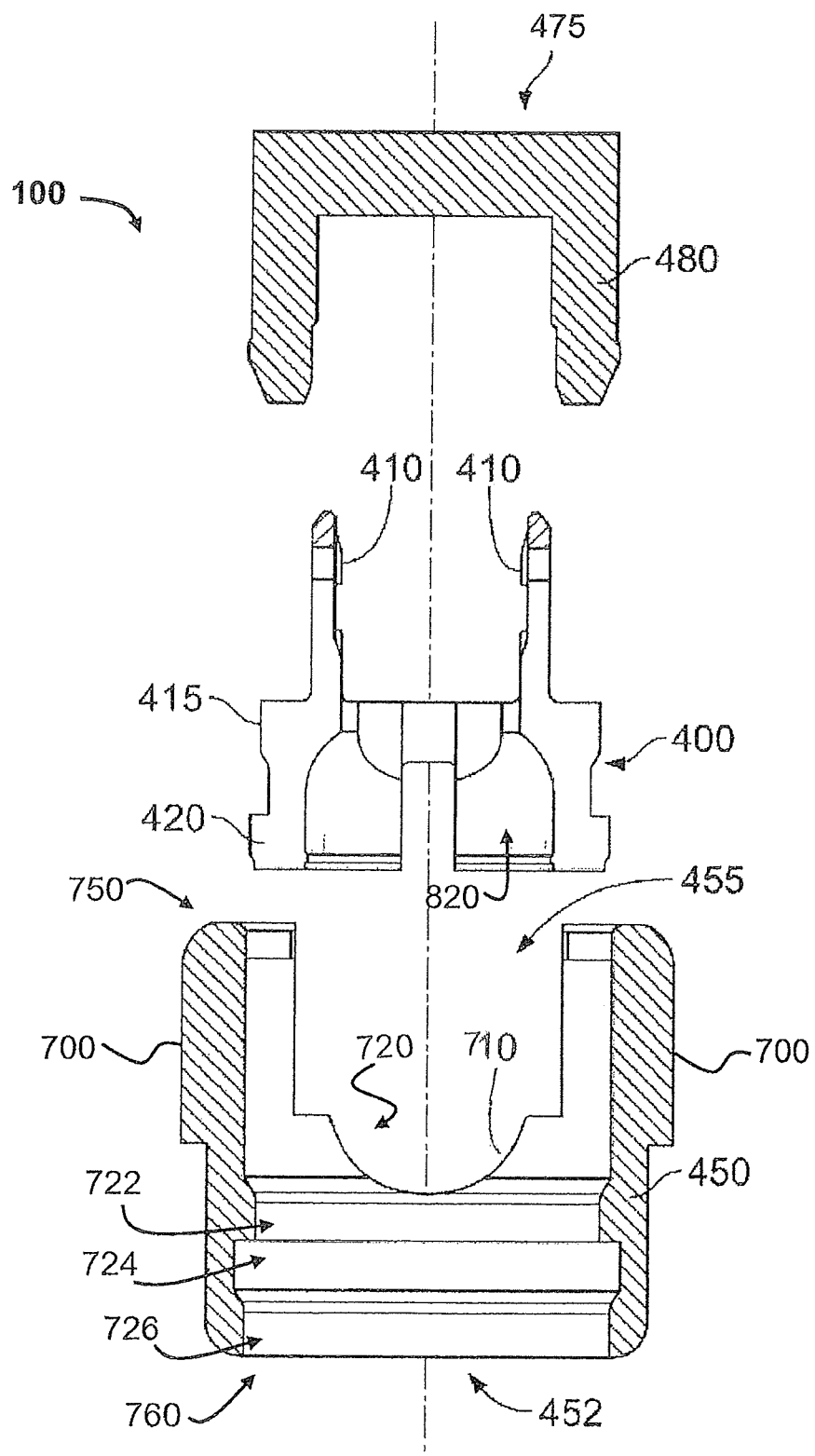
FIG. 2 is a front exploded cross-sectional view of the pedicle screw system of FIG. 1.
Figure 3:
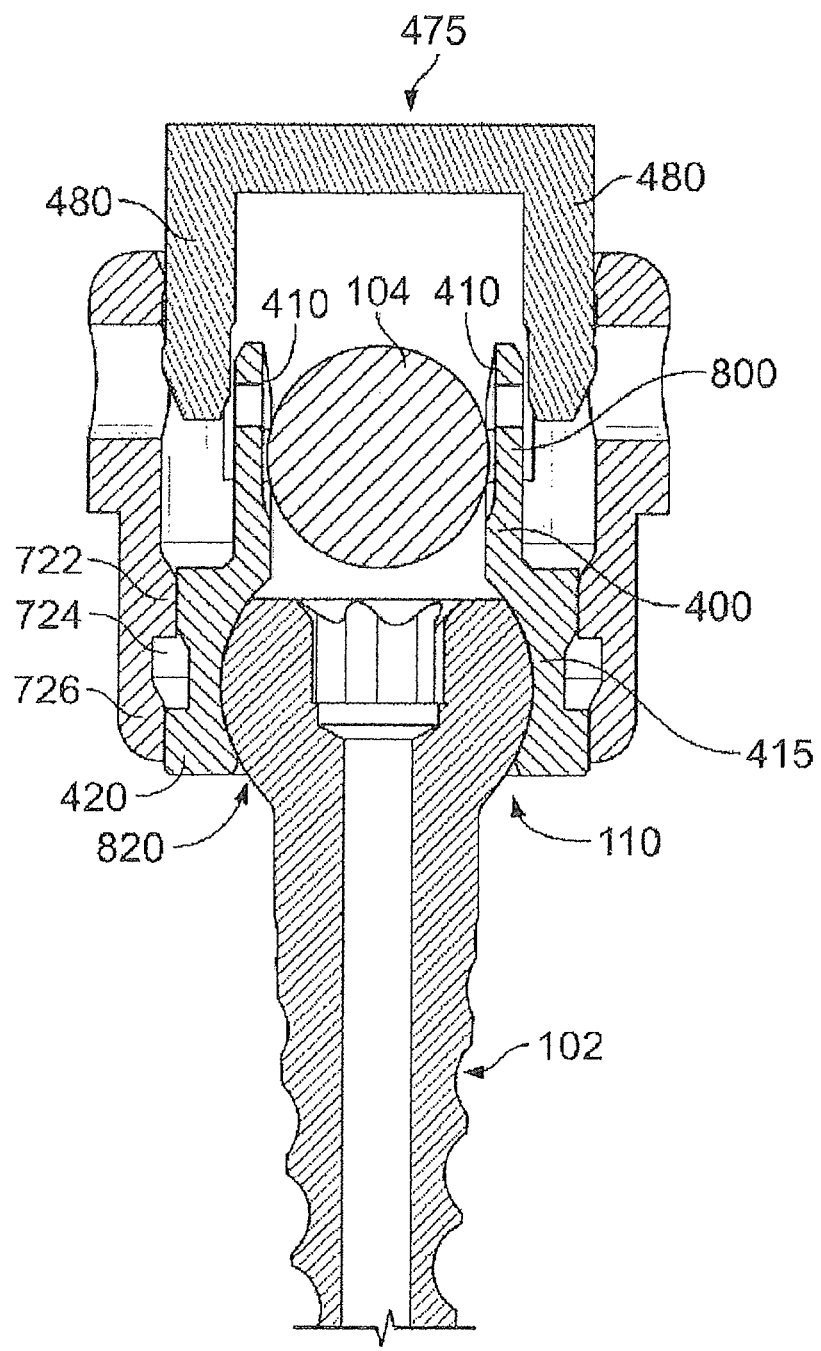
FIG. 3 is a front view of the components of a pedicle screw system as in FIG. 1, with the pedicle screw locked in place and a compression cap partially inserted and snapped into place.

FIGS. 1-3 illustrate a basic coupling assembly structure capable of locking an anchor member to a rod via the linear shifting of an outer member and an insert member. As described further herein, these structures may be modified to allow for a provisional or partial lock configuration to better retain a pedicle screw prior to full locking of the assembly.

FIG. 1 illustrates a front (along the axis of a captured spinal rod) exploded view of an exemplary coupling assembly 100, including an outer member or body 450 and an insert member 400, as well as an exemplary rod lock member 475. FIG. 2 shows a cross-sectional view of the assembly.

As shown, the insert member 400 may include a number of functional features including, but in no way limited to a plurality of spaced apart rod engagement members or arms 410 configured to receive a spinal rod. Additionally, a proximal locking feature 415 and a distal locking feature 420 may be formed on the outer surface of the insert member 400 in order to interact with the outer member 450 and selectively capture the head 110 of a pedicle screw 102. Alternatively, the exterior of the insert member may have other profiles or features, as long as it is configured to interact with the interior of the outer member 450 to lock onto a pedicle screw. The locking features 415 and 420 shown are formed as annular flanges extending from the lower portion of the insert member 400. The exemplary illustrated compression cap 475 includes a plurality of compression protrusions in the form of legs 480 that cooperate with the insert 400 and outer member 450 to lock the rod. As shown in FIG. 2, the outer member 450 and insert member 400 include a number of elements that facilitate the ability to separately lock both the positions of the pedicle screw 102 and a rod 104 relative to the coupling assembly 100. According to one exemplary embodiment, the outer member 450 includes an internal space 452 in the form of a throughbore, a proximal end 750, a distal end 760, a rod reception recess 455 defined by upright side walls 700, and a number of internal annular features 722, 724, and 726 configured to allow for the selective compression and expansion of an insert member.

According to one exemplary embodiment, the bore 452 is configured to permit assembly of the outer member and insert before being placed onto the head portion of the pedicle screw. In one embodiment, the insert member 400 of the coupling assembly may be inserted into the outer member 450 through the bore 452. Once the coupling assembly 100 is pre-operatively assembled, a wide portion 724 of the outer member interior space facilitates reception of the head portion 110 of the pedicle screw 102 within the insert member 400 by permitting the insert member lower portion to expand.

The outer member 450 is illustrated as a generally cylindrical member having a plurality of side walls 700 extending toward the proximal end 750 of the outer member. According to one exemplary embodiment, the plurality of side walls 700 define both the proximal portion of the throughbore 452 and the rod recess 455 including a rod stop surface 710. The rod stop surface may be contoured to match the outer surface of the rod. In the illustrated assembly, the proximal portion 750 of the outer member 450 is open to receive a spinal rod. As mentioned, the rod 104 may be inserted into the outer member 450 either before or after placement of the coupling assembly 100 on the head portion 110 of the pedicle screw 102. Initially, the rod 104 is received by both the insert member 400 and the outer member 450 via the rod recess 455. Consequently, according to one exemplary embodiment, the width of the rod recess 455 may be substantially equal to or greater than the diameter of a desired rod 104. However, according to other exemplary embodiments, the rod recess 455 may be slightly narrower than the diameter of a desired rod 104 to allow for a slight interference fit during insertion. Once the rod 104 is received by the outer member 450 and the insert member 400 via the rod recess 455 the lateral motion of the rod is limited by the sidewalls 700 and/or the upright arms 410 of the insert member, and in some embodiments the vertical position of the rod may be limited, at least in part, by the rod stop surface 710.

The outer member 450 of FIG. 2 also includes a number of elements that allow the relative angular position of the coupling assembly 100 to be independently established relative to the pedicle screw. Specifically, the internal wall of the outer member 450 defining the throughbore 720 can include, according to one exemplary embodiment, a proximal annular compression feature or locking feature 722, a distal annular compression feature or locking feature 726 and an annular expansion groove 724. According to one exemplary embodiment, the proximal and distal annular compression features 722, 726 are configured to interact with the proximal locking feature 415 and distal locking feature 420 (FIG. 1) of the insert member to compress the insert member about the head portion of the pedicle screw, thereby fixing the relative angular position of the coupling assembly relative to the pedicle screw. Additionally, one or more slits in the insert member lower portion may be provided to permit selective expansion of the insert member 400 to facilitate reception of the head portion 110 of the pedicle screw when the distal annular locking feature is positioned in the annular groove of the outer member, as will be described in detail below. While the present figures and description describe the internal compression and expansion features as annular protrusions and recesses, any number of selectively disjointed, or varying protrusions or recesses may be used to allow selective expansion and compression of the insert member 400. Additionally, the insert member and outer member may even have continuous tapered surfaces designed to compress the insert during linear travel of the insert into the outer member.

Figure 5:
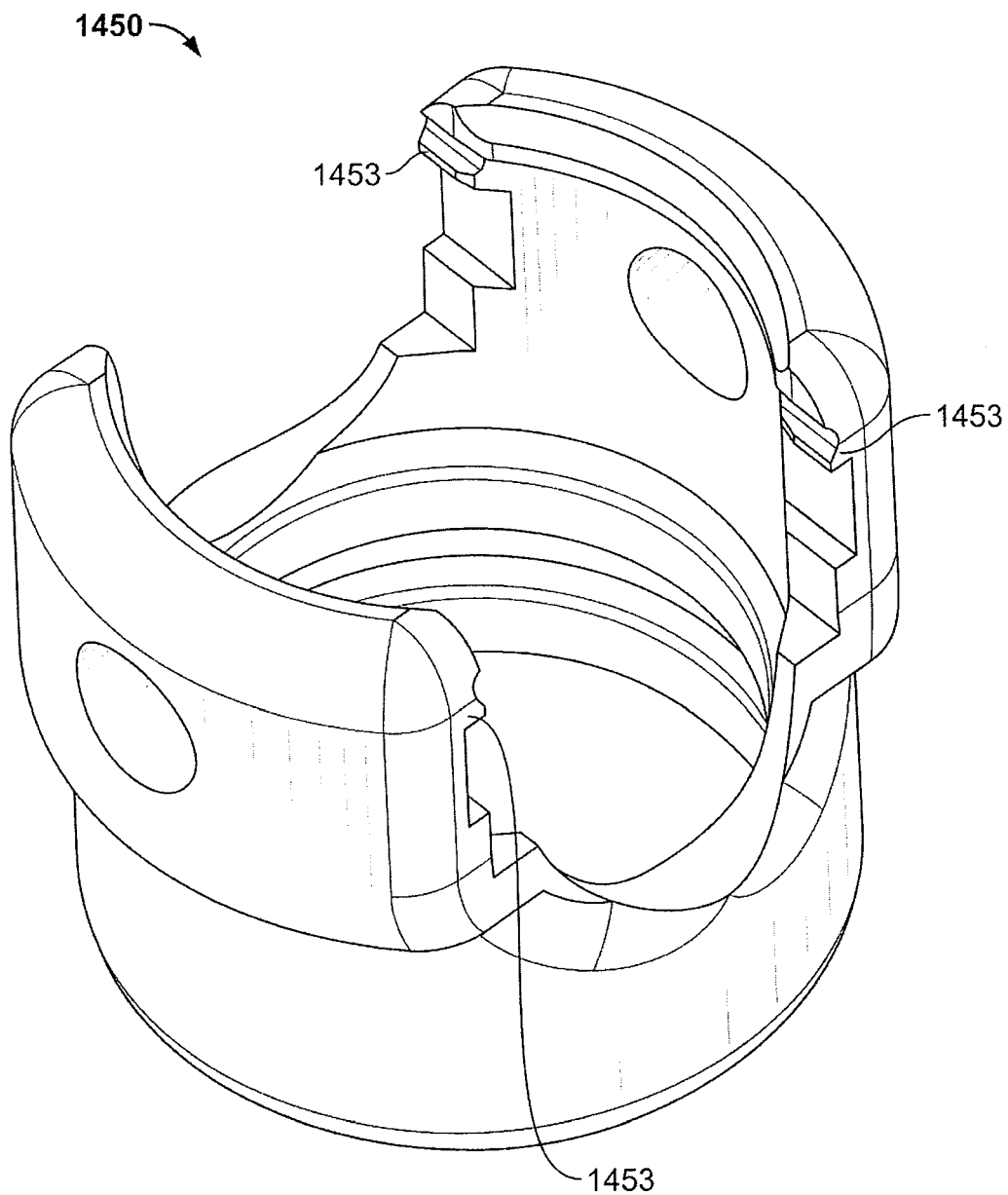
FIG. 5 is a perspective view of an exemplary embodiment of an outer member with inwardly-facing retention features and with bores in its side surfaces for receiving an instrument.

The exterior of the outer member may contain features to interact with tools designed to implant and operate the assembly. For instance, as shown in FIG. 5, an outer member may contain radially-directed bores or openings so that portions of an instrument may transversely engage and grip the outer member and be used to position the outer member during implantation or shifting of the outer member relative to the insert member during locking.

FIG. 3 shows a cross-sectional view of the coupling assembly with an associated rod 104 and anchor member. The anchor member, such as pedicle screw 102, is received in the insert member 400, for instance by snap-locking. The screw 102 is still able to pivot with respect to the insert 400. When a desired orientation of the screw 102 relative to the insert 400 is established, the coupling assembly position relative to the pedicle screw may be locked by shifting the insert member relative to the outer member 450. Locking can be obtained by either pulling up on the outer member 450 and/or pushing down on either the rod 104 or the insert member 400. Locking is obtained by shifting of the outer member relative to the insert member to create an interference fit between the proximal locking feature 415 and the distal locking feature 420 of the insert member 400 and the proximal annular compression feature 722 and the distal annular compression feature 726 of the outer member 450, respectively. When these mating features are engaged, the head receiving orifice 820 of the insert is compressed about the head portion 110 of the pedicle screw 102.

It is understood that the relative angular position of a first coupling assembly 100 to a first pedicle screw 102 may be different from the relative orientation of other pedicle screw systems located elsewhere on a patient's spine. In general, the relative, angular position of the coupling assembly 100 to the pedicle screw 102 allows the surgeon to selectively and independently orient and manipulate the coupling assemblies 100 of each pedicle screw system 100 installed into the patient to achieve and/or optimize the goals of the surgical procedure, which may involve compressing, expanding, distracting, rotating, reinforcing, and/or otherwise correcting an alignment of at least a portion of a patient's spine. According to one exemplary embodiment, when the proximal locking feature 415 and the distal locking feature 420 of the insert member 400 are engaged with the proximal annular compression feature 722 and the distal annular compression feature 726 of the outer member 450, respectively, the frictional force exerted on the head portion 110 of the pedicle screw 102 is maintained, locking the assembly in a desired position with respect to the screw.

With the assembly position relative to the pedicle screw established due to the positioning of the insert member 400, a rod lock member may be used to secure the rod. The rod lock member may be, for instance, a linearly-inserted compression cap, but a variety of other configurations are also possible. As illustrated in FIG. 3, a compression cap 475 is snapped into the coupling assembly 100 but is not fully seated. The partial insertion of the illustrated compression cap 475 fills in the gap between the rod retention arms 800 of the insert member 400 and the outer member 450, preventing the insert member from expanding. Consequently, the rod 104 is retained within the insert member 400 and the outer member 450 by an increased pressure or frictional force being applied at the interface between the rod engagement ridges 410 and the rod 104. When the positioning of all of the related components is confirmed, complete insertion of the compression cap 475 may be performed for a final lock of the rod. Completely seating the illustrated compression cap 475 compresses the rod retention protrusions 800 of the insert member 400 to grip the rod 104. Additionally, the insertion of the compression cap 475 may be configured to prevent the outer member 450 from splaying open under operative and post-operative dynamic and static loading, for example. Splaying is prevented due to the material that is coupled up and over the rod 104 by the compression cap 475.

With this type of pedicle screw system, the surgeon has the ability to check and even double check the placement, angle, and/or orientation regarding aspects of the pedicle screw system to facilitate, and even optimize, the compression, distraction, and/or other manipulation of the spinal segments. In contrast, many prior art pedicle screw assemblies are designed such that a cap member designed to secure the rod in place also acts to force the rod downward onto the head of a pedicle screw, clamping the screw head against a bottom surface of the assembly and locking the position of the screw simultaneously with locking the position of the rod. A disadvantage of these prior art pedicle screw systems is that the assembly pivots freely upon the head of the pedicle screw until the rod is secured in the assembly and locked into place against the screw head. In the system of FIGS. 1-3, the cap and outer member may be shifted simultaneously in order to simultaneously lock the screw and rod into position, but the screw may also be locked into position prior to the rod being received in the coupling assembly.

One possible post-operative advantage of the present exemplary pedicle screw system is that the cooperation and interaction of the insert member 400 with the compression cap 475 substantially reduces, and most likely prevents, the known problem of the assembly splaying. Assembly splaying is generally regarded as a post-operative problem caused by a stressed rod forcing open portions of the outer member, which eventually leads to the disassembly and likely failure of the pedicle screw system within the patient. Yet another post-operative advantage of the pedicle screw systems is that unlike existing rod-coupling members or constructs, the exemplary coupling assemblies described herein have a smaller size envelope (e.g., are less bulky, have a lower profile, and/or are more compact in shape) and are easier to place onto the pedicle screw when compared to traditional systems. The smaller size and ease of installation may reduce trauma to the soft-tissue regions in the vicinity of the surgical site, which in turn generally allows for a quicker recovery by the patient. According to aspects described herein, and as appended by the claims, the present exemplary pedicle screw systems permit insertion of the pedicle screw without the coupling assembly coupled thereto, locking the coupling assembly onto the pedicle screw, and subsequently capturing and locking the rod into the assembly.

Screw systems such as the one shown in FIGS. 1-3 and other systems including an insert member that couples to an anchor member and then is inserted into an outer member for locking may be modified as described herein to better retain and/or provisionally lock the anchor member. It is desirable in some circumstances to implement additional features to strengthen the mating relationship between the coupling assembly and the pedicle screw or other anchor member prior to final locking, since after implantation it is often necessary to apply significant amounts of force in order to rotate and shift the coupling assemblies into alignment with each other or into alignment with spinal rods. Retention features may be added to prevent the screw head from escaping the cavity in the lower portion of the coupling assembly when in a provisional screw lock position prior to full screw locking, allowing the coupling assembly to be pivoted about the screw head but preventing the screw head from separating from the coupling assembly.

Figure 4A:
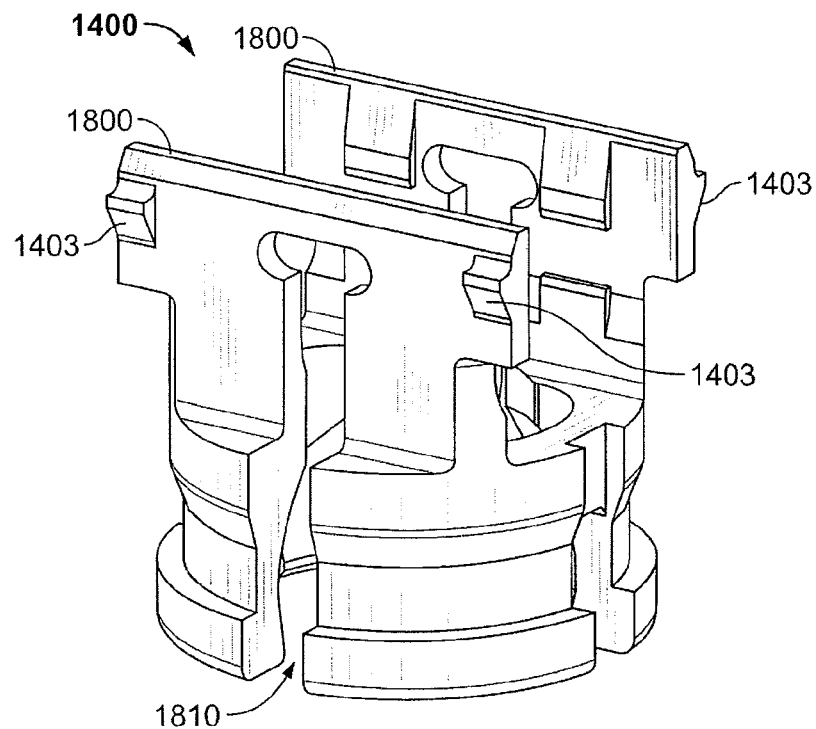
FIGS. 4A and 4B are perspective views of one exemplary embodiment of an insert member with retention features to limit axial shifting of the insert member with respect to an outer member.
Figure 4B:
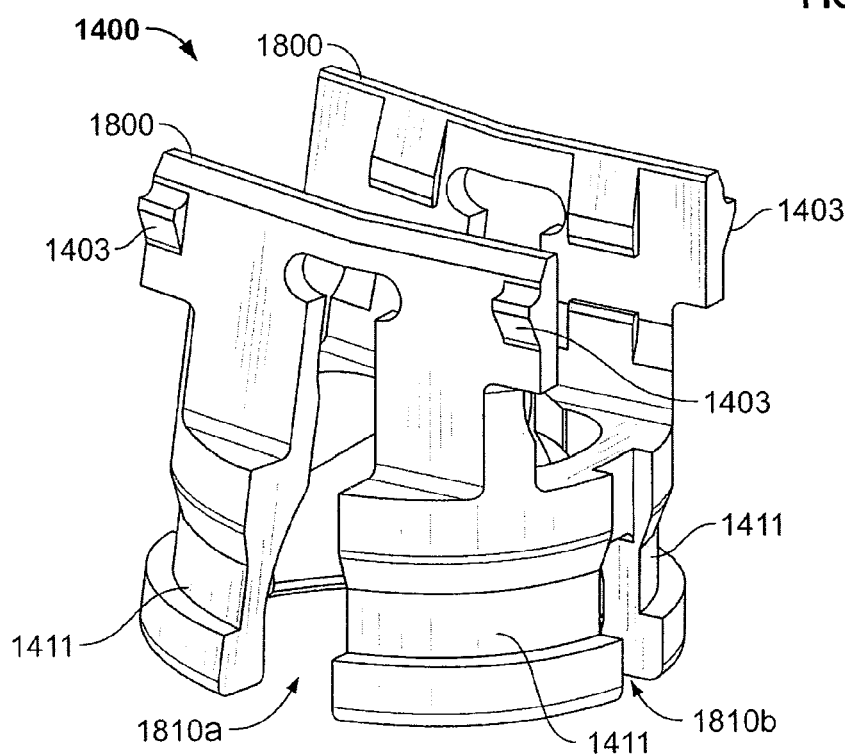

In one form, the insert member and outer member may be provided with features to limit axial or other linear movement with respect to each other prior to full locking, allowing for one-way locking of the insert member and outer member and preventing the insert member from backing out of the outer member once inserted to a predetermined position. For example, the embodiment depicted in FIGS. 4-8 has one-way retention elements in the form of outwardly-extending inclined retention tabs 1403 on the insert member 1400 (FIGS. 4A-B) and complementary inwardly-extending inclined retention tabs 1453 on the outer member 1450 (FIG. 5). The outer member retention tabs 1453 are positioned to engage the inner member retention tabs 1403 when the inner member shifts axially within the outer member 1450. As shown in one exemplary embodiment in 17A, the insert tabs 1403 may protrude from the flexible arms 1800 of the rod-retaining portion of the insert. In this position, the tabs do not shift inward as portions of the annular wall 1411 of the lower portion flexes, as shown in FIG. 4B, since the flexible arms 1800 are transverse to the major expansion gaps 1810a primarily responsible for flexion of the annular wall portions 1411 and expansion of the cavity formed thereby. Minor expansion gaps 1810*b* in the annular wall 1411 of the insert 1400 have a shorter length in the axial direction than the major expansion gaps, and therefore do not provide for the same amount of flexion of the annular wall 1411 as the major expansion gaps 1810*a*.

Figure 6A:
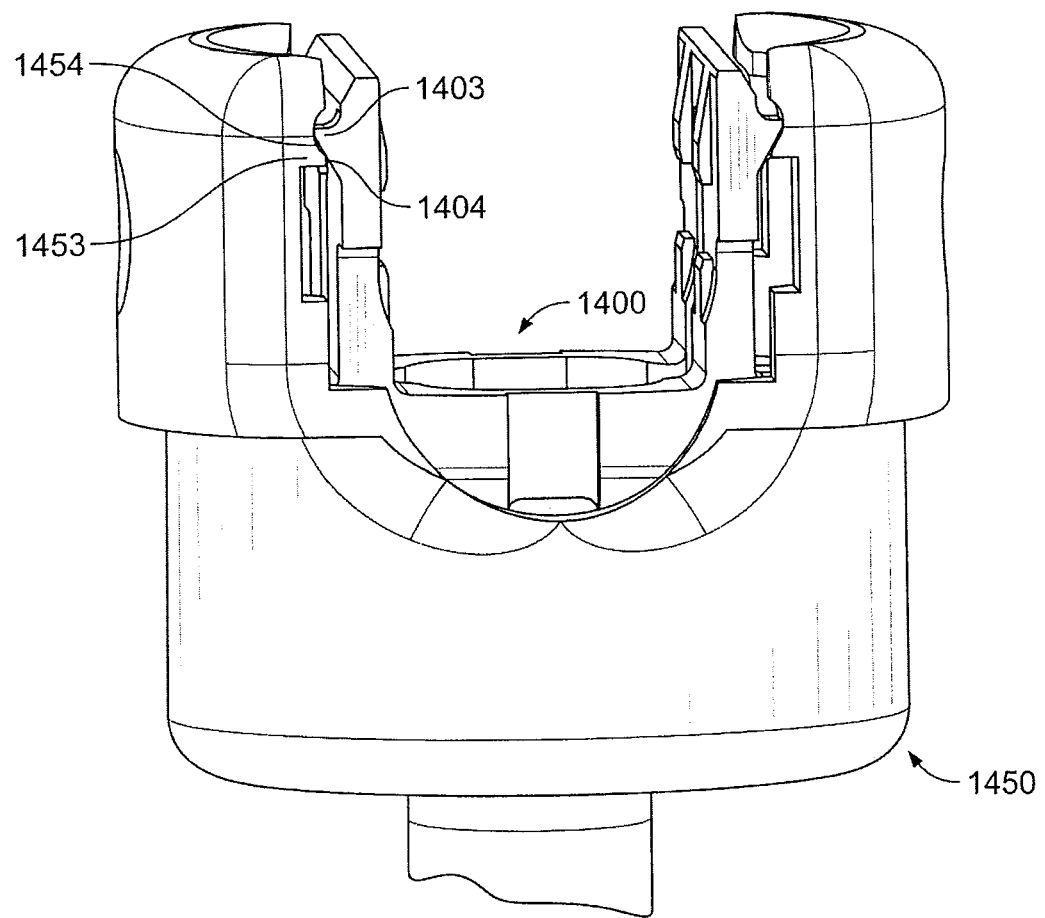
FIGS. 6A and 6B are a front view and a front cross-sectional view, respectively, of a coupling assembly, and retention features thereof, in a screw-receiving configuration.
Figure 6B:
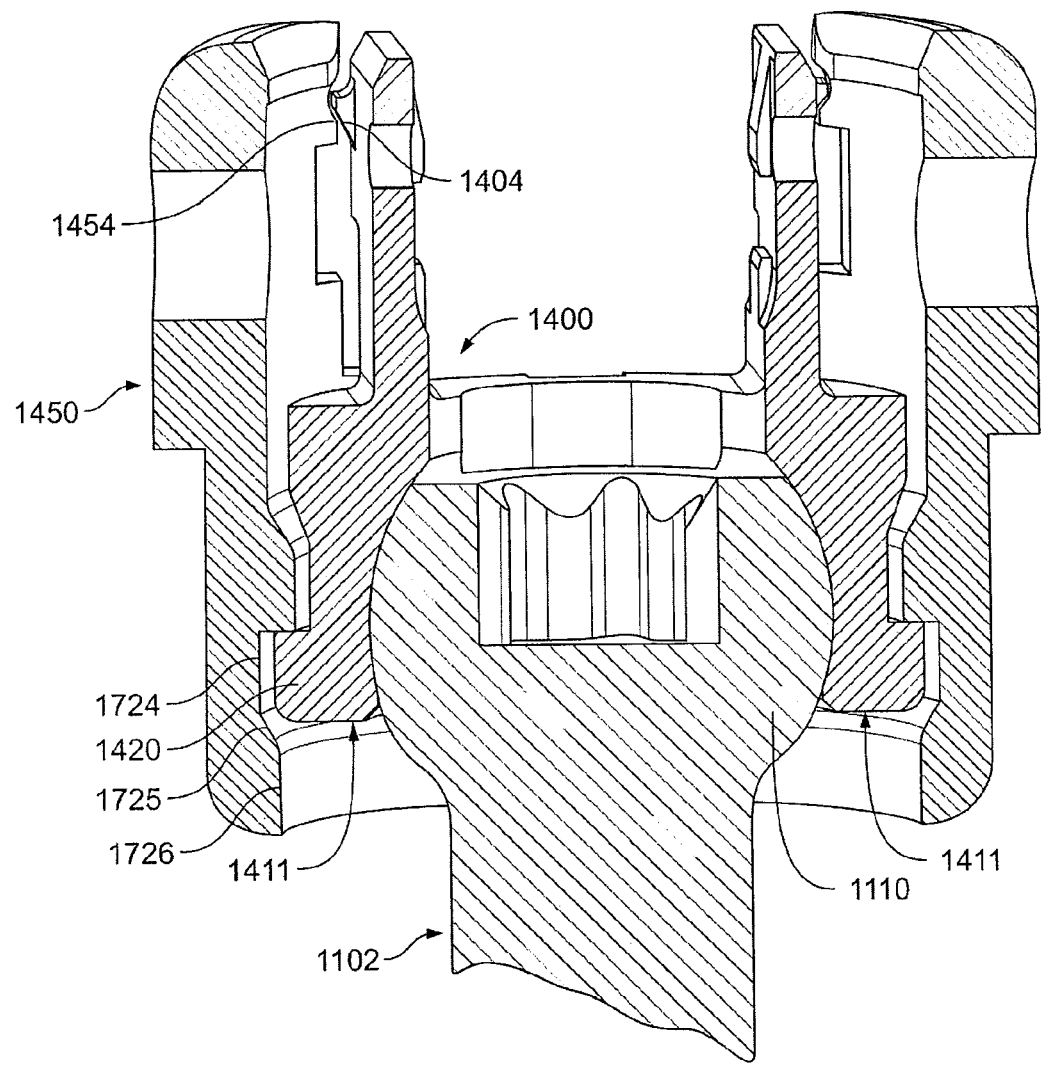

The insert 1400 is shown in FIGS. 6A-B in an initial position within the internal space of the outer member 1450, wherein the retention tabs 1403 on the insert and retention tabs 1453 on the outer member do not interfere with one another. Downward-facing inclined surfaces 1404 of the insert 1400 are facing toward complementary upward-facing inclined surfaces 1454 on the outer member 1450. As shown in FIG. 6B, when the annular flange or locking feature 1420 of the insert member is positioned within the annular groove 1724 of the outer member, a sufficient amount of force will dislodge screw head 1110 from the insert member by shifting the annular wall portions 1411 of the insert member 1400 outward, creating an opening large enough for the screw head 1110 to escape. Consequently, the insert member 1400 and outer member 1450 may be pre-assembled in this position, and the pedicle screw 1102 may be inserted and removed from the assembly relatively easily. The locking feature 1420 of the annular wall is allowed to shift outward because it is positioned in an annular expansion recess 1724 sized to allow for expansion of the insert member.

Figure 7A:
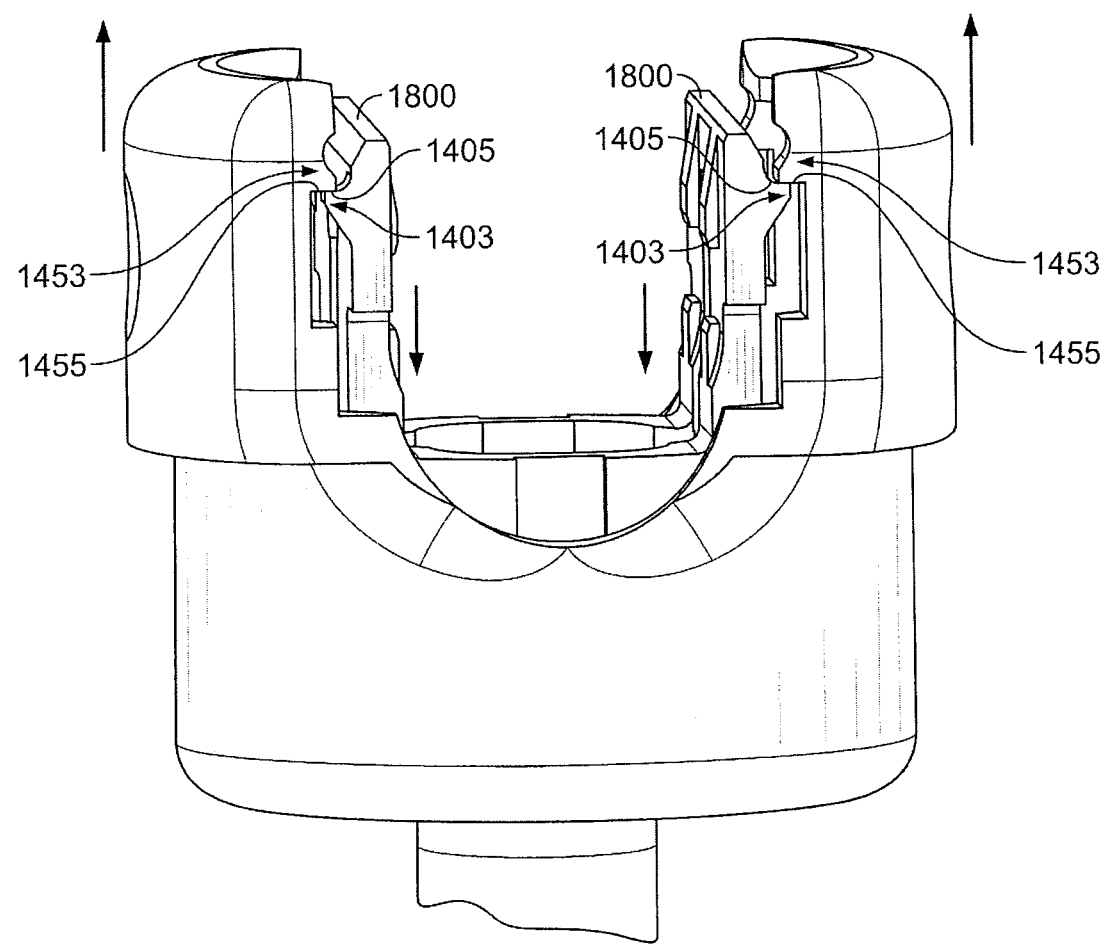
FIGS. 7A and 7B are a front view and a front cross-sectional view, respectively, of a coupling assembly in a screw-retaining or provisional locking configuration.
Figure 7B:
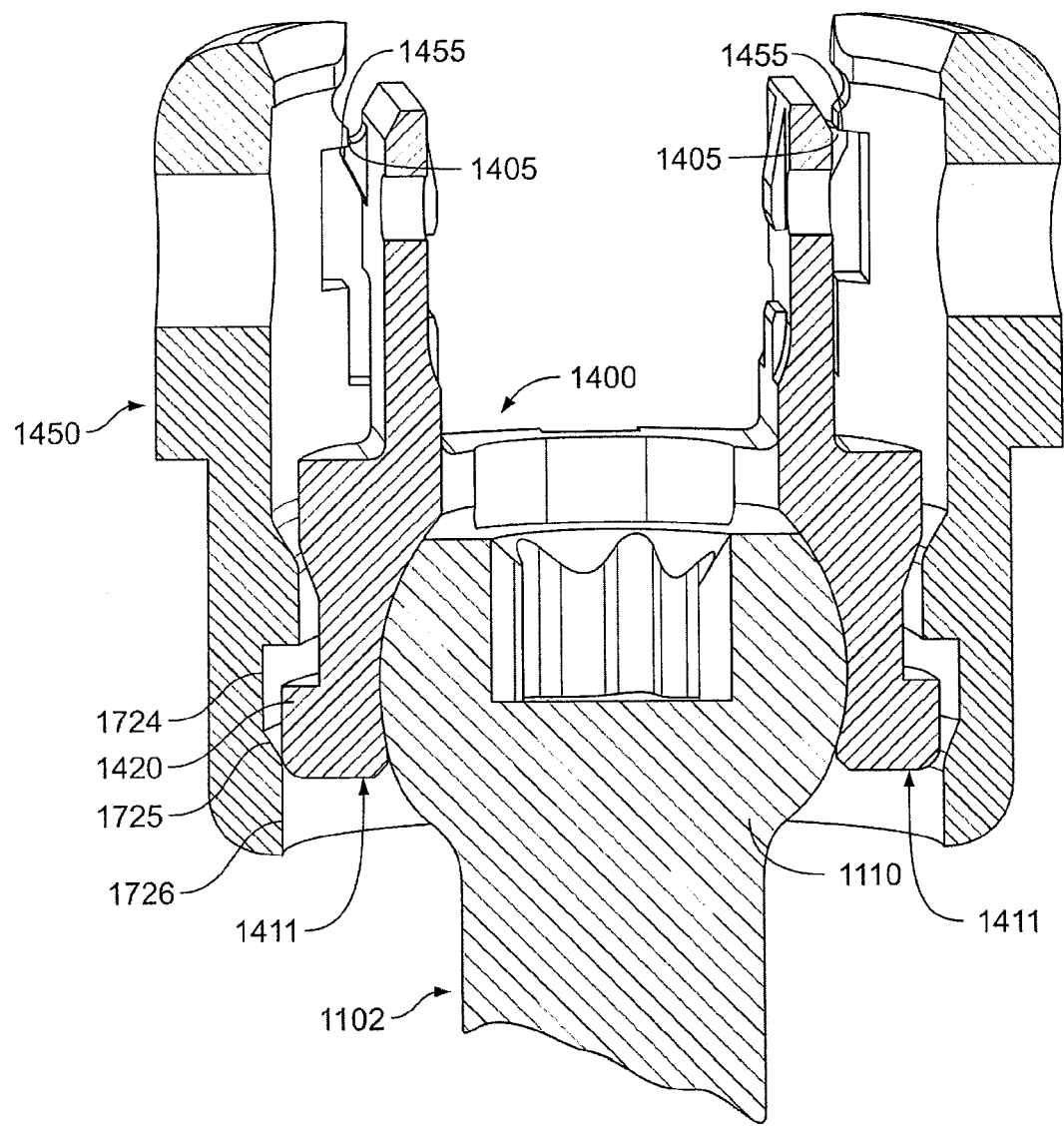

As the outer member 1450 is pulled upward relative to the insert member 1400 (so that the insert member 1400 shifts downward within the interior space of the outer member), the downward-facing inclined surfaces 1404 of the insert retention tabs 1403 engage the complementary upward-facing inclined surfaces 1454 on the outer member retention tabs 1453, and because of their complementary inclined surfaces the tabs 1403 and 1453 slide past one another. Flexible portions 1800 shift slightly inward to allow the retention tabs to slide past one another. Eventually, the insert member retention tabs 1403 are shifted to a retention position wherein the insert member retention tabs 1403 are located below the outer member tabs 1453, as shown in FIGS. 7A-B. Reaching this retention position may provide an audible click or other feedback as the insert member tabs 1403 slide past the outer member tabs 1453, allowing the flexible arms 1800 to shift slightly outward to their original positions, snapping the insert member tabs 1403 into place below the outer member tabs 1453.

In this retention position, the insert member is permitted to shift further downward into the outer member 1450, but resists shifting upward because of flat abutment surfaces 1405 and 1455 on the trailing ends of the tabs. As shown in FIG. 7B, the tabs are positioned axially along the insert member and outer member so that when the tab abutment surfaces 1405 and 1455 meet, the annular camming locking feature 1420 of the lower portion of the insert member 1400 begins to engage a locking feature 1726 inside the outer member 1450, causing the annular wall 1411 of the insert member 1400 to compress and shift slightly inward, applying a frictional force upon the screw head 1110. For instance, as depicted, a tapered cam surface 1725 leads to the locking feature 1726, causing gradual compression of the lower annular wall 1411 of the insert member 1400. In the position depicted in FIG. 7B, the compressive force exerted against the lower portion of the insert member 1400 by the tapered camming surface 1725 is sufficient to prevent the screw head 1110 from exiting the cavity formed by the annular wall 1411 of the insert member 1400, but will not fully lock the coupling assembly against pivoting with respect to the screw head 1110. The insert assembly 1400 resists backing out from this retention position due to the interaction between the abutment surfaces 1455 of the outer member tabs 1453 and the abutment surfaces 1405 of the insert member tabs 1403.

Figure 8A:
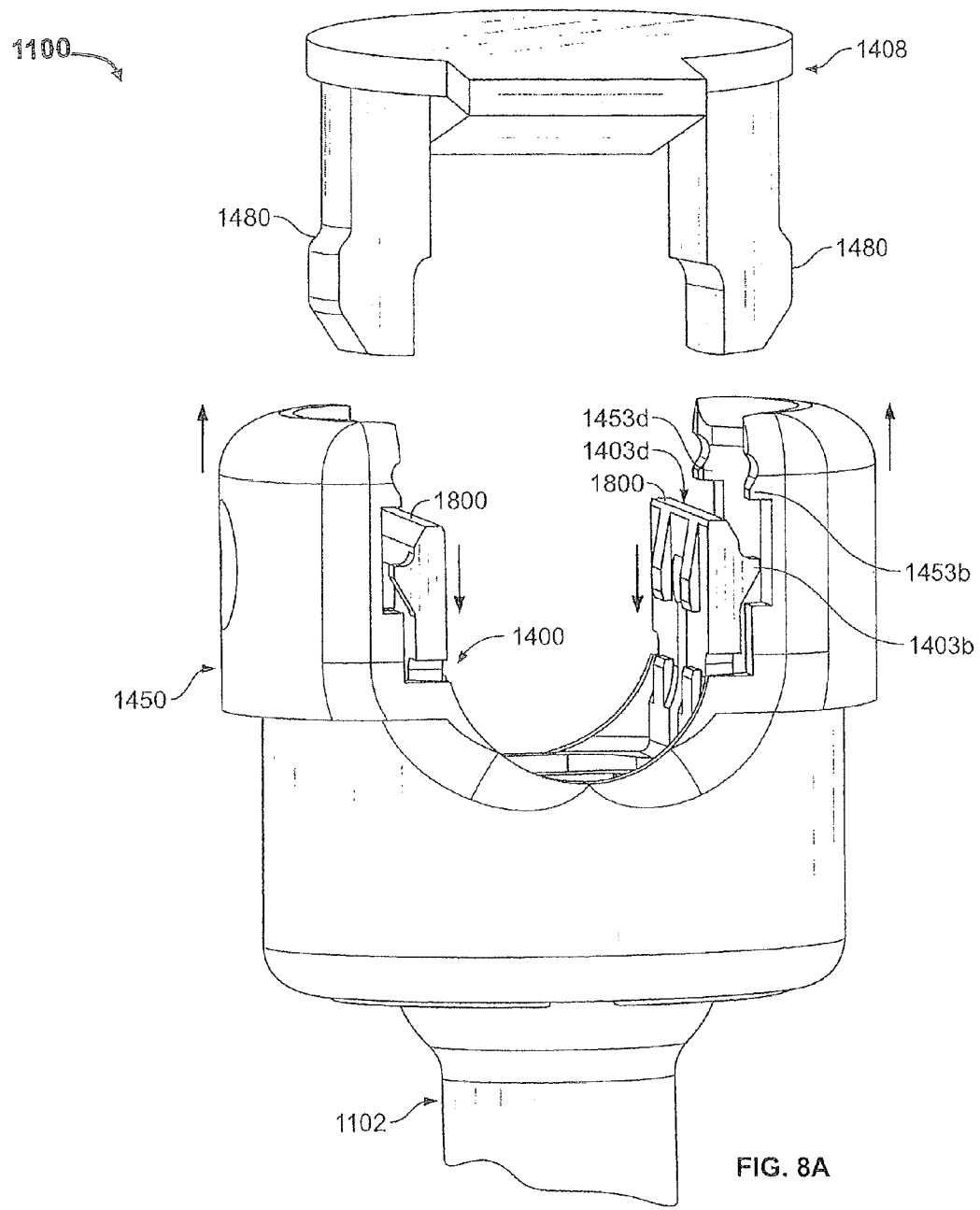
FIGS. 8A and 8B are a front view and a front cross-sectional view, respectively, of a coupling assembly in a screw-locking configuration.
Figure 8B:
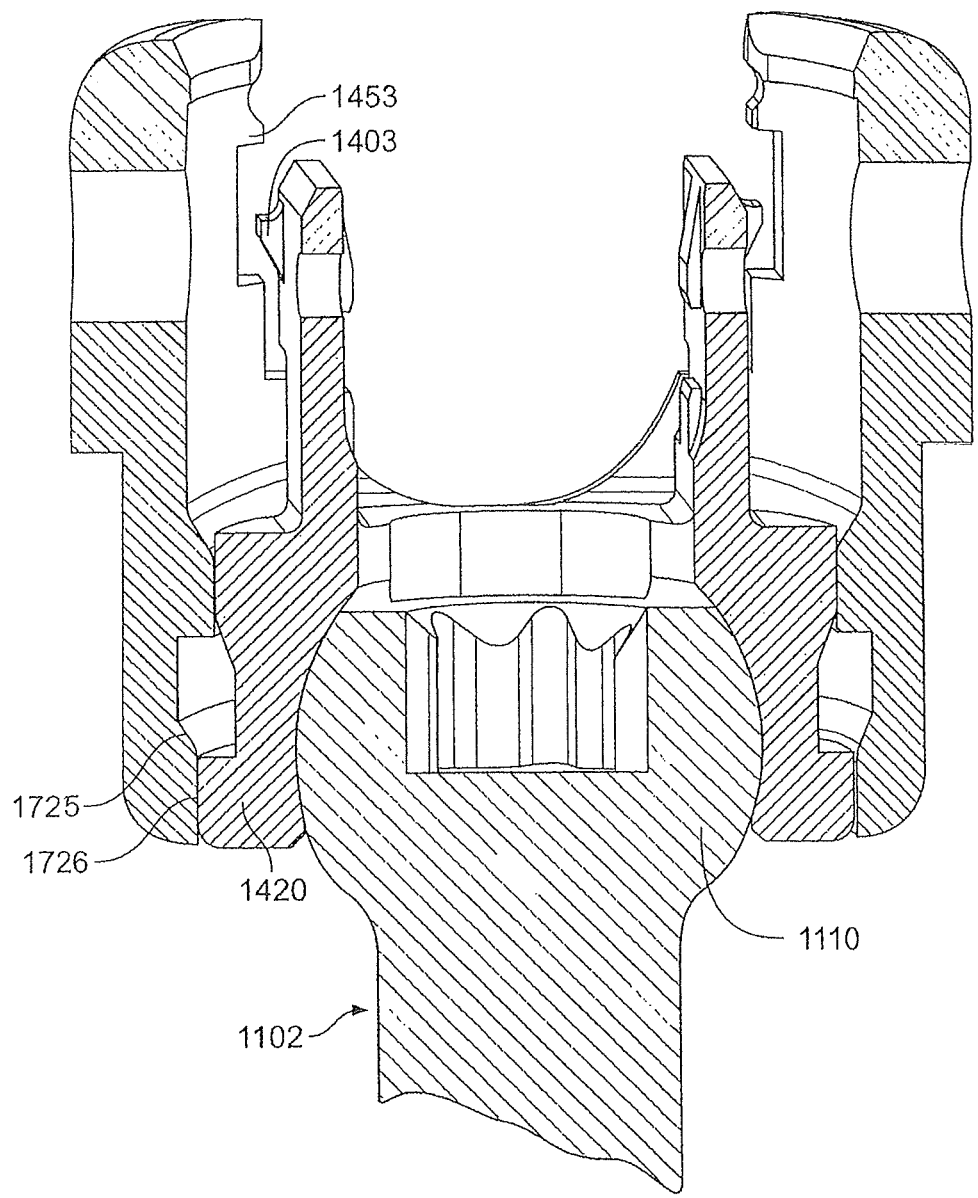

Full locking of the screw head 1110, which prevents changes in angulation between the coupling assembly 1100 and screw 1102, is achieved again by pulling upward on the outer member 1450 as shown in FIG. 8A (further shifting the insert member 1400 downward relative to the interior of the outer member) so that the camming locking feature 1420 moves past the tapered cam surface 1725 of the outer member bore and into flush contact with the inwardly-directed face of the annular locking feature 1726 at the bottom of the bore, as depicted in FIG. 8B. In this full locking position, the insert member retention tabs 1403 are spaced below the outer member retention tabs 1453 so that the tabs no longer interact. Pairs of interacting tabs (for instance, first pair of tabs 1403*b*, 1453*b* and second pair of tabs 1403*d*, 1453*d* depicted in FIG. 8A) are spaced far enough apart in a direction parallel to the rod axis (which is generally orthogonal to the outer member axis) to allow locking portions 1480 of a rod locking device such as cap 1408 to slide axially into engagement with the flexible arms 1800 of the insert member to deflect the flexible arms 1800 inward and lock the rod in place, as previously described.

In another form, retention of the screw head prior to full locking may be enhanced by configuring the coupling assembly and screw head so that the screw head is inserted into the cavity of the insert member in one orientation and shifted or rotated to a second orientation to resist withdrawal of the screw head from the cavity. For instance, as depicted in FIGS. 9-12, a screw 2102 is provided having a head portion 2110 with a height ("h"), a first head width ("x") and a second head width ("y"), where the first head width is larger than the second head width. In this manner, the head is sized and shaped so that it may enter and exit the cavity of the insert member more easily in one orientation than in another orientation. The form of screw head depicted in FIGS. 9A-C forms essentially a truncated sphere, with a partially spherical profile when viewed from one transverse direction (FIG. 9B) and a wedge-shaped profile when viewed from a second transverse direction (FIG. 9C). This wedge shape facilitates alignment and insertion of the screw head with the opening in the insert member for snap-locking therein.

Figure 9A:
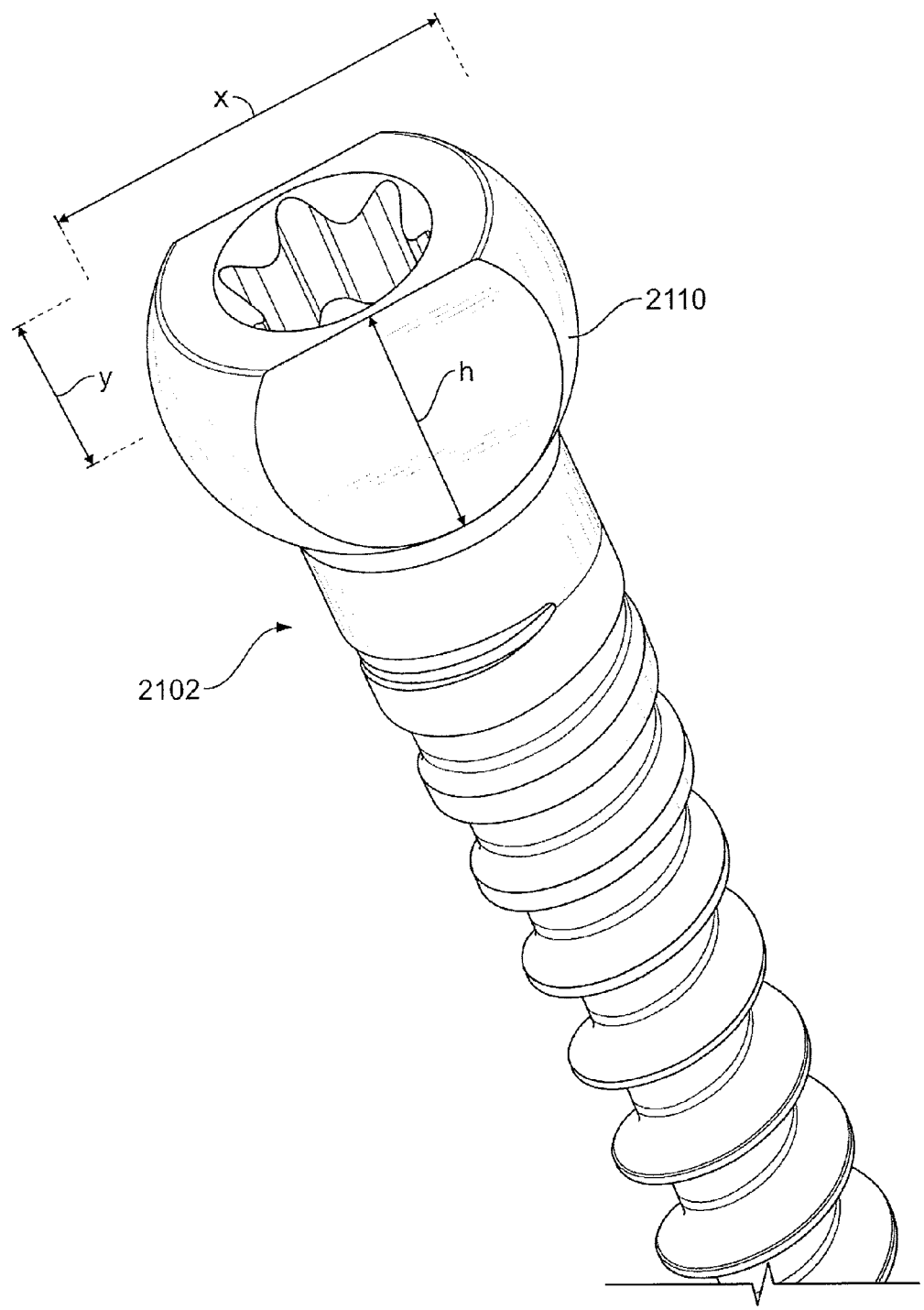
FIGS. 9A-9C are perspective views of an exemplary alternative bone anchor in the form of a pedicle screw having a truncated spherical head portion.
Figure 9B:
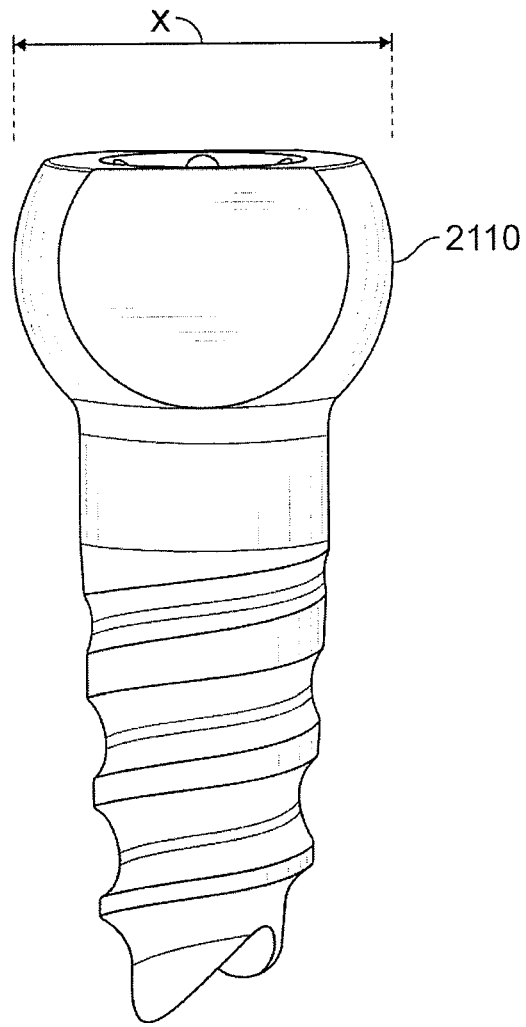
Figure 9C:
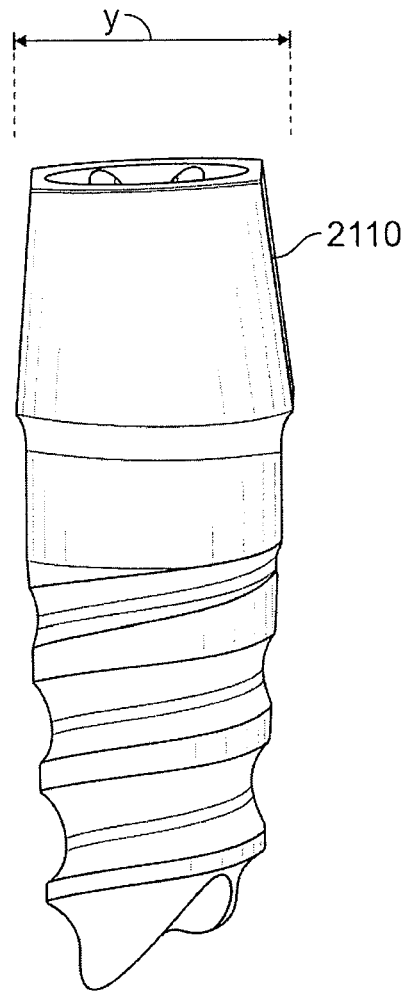
Figure 10A:
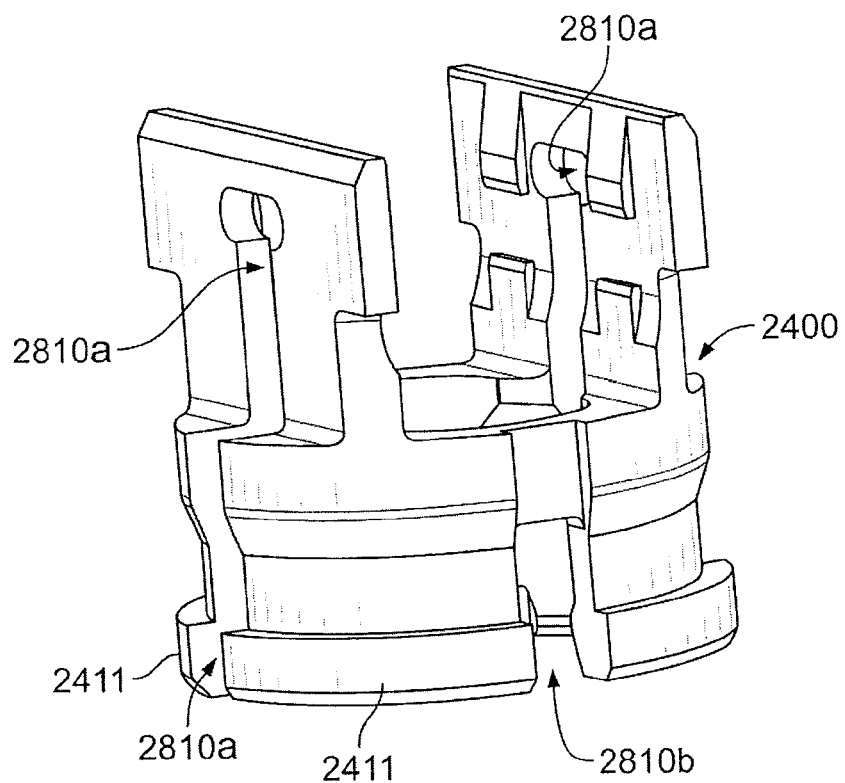
FIGS. 10A and 10B are a perspective and bottom plan view, respectively, of an exemplary insert member configured to receive the alternative bone anchor of FIG. 9.
Figure 10B:
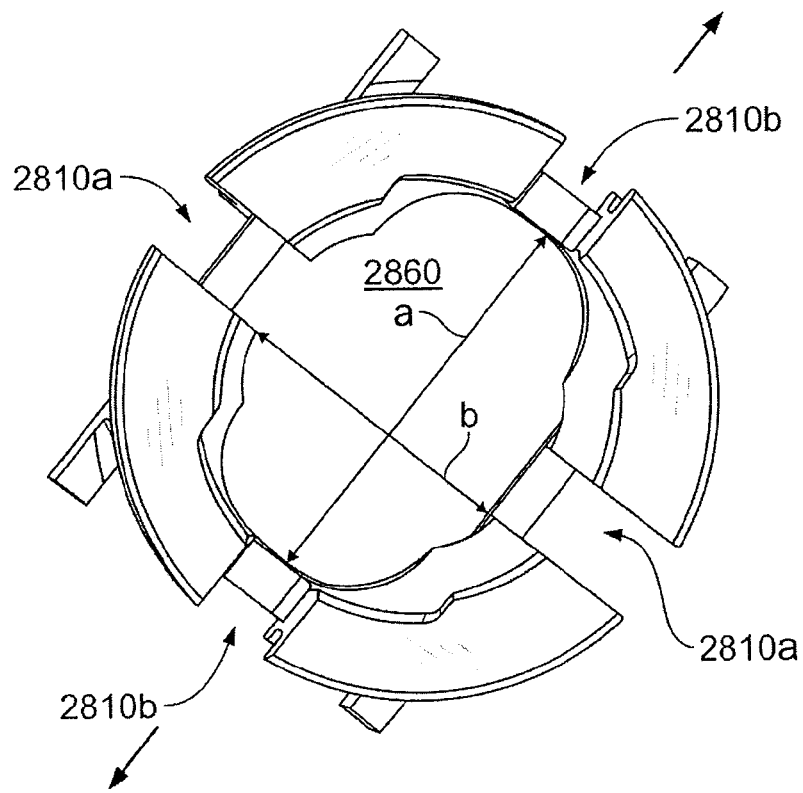

The screw head of FIGS. 9A-C is received in a complementarily configured insert member 2400, depicted in FIGS. 10A and 10B. As with other exemplary insert members described herein, the insert member includes expansion gaps 2810 for allowing the annular wall portions 2411 of the insert member to flex for receiving a screw head therebetween in a snap-lock manner. As with other embodiments, the expansion gaps 2810 also allow the annular wall portions 2411 to be compressed or compacted, applying a frictional force onto the screw head to lock it in place. Major expansion gaps 2810*a* allow for relatively large amounts of flexion due to their length, while minor expansion gaps 2810*b* permit relatively less flexion. As shown in FIG. 10B, an opening 2860 in the lower portion of the insert member is configured to receive a screw head. The opening 2860 has a first width ("a") that is larger than a second width ("b"). The first, longer width lies transverse to the major expansion gaps 2810*a*, so that the insert member lower portion widens in the direction of the greater opening width ("a").

Figure 11A:
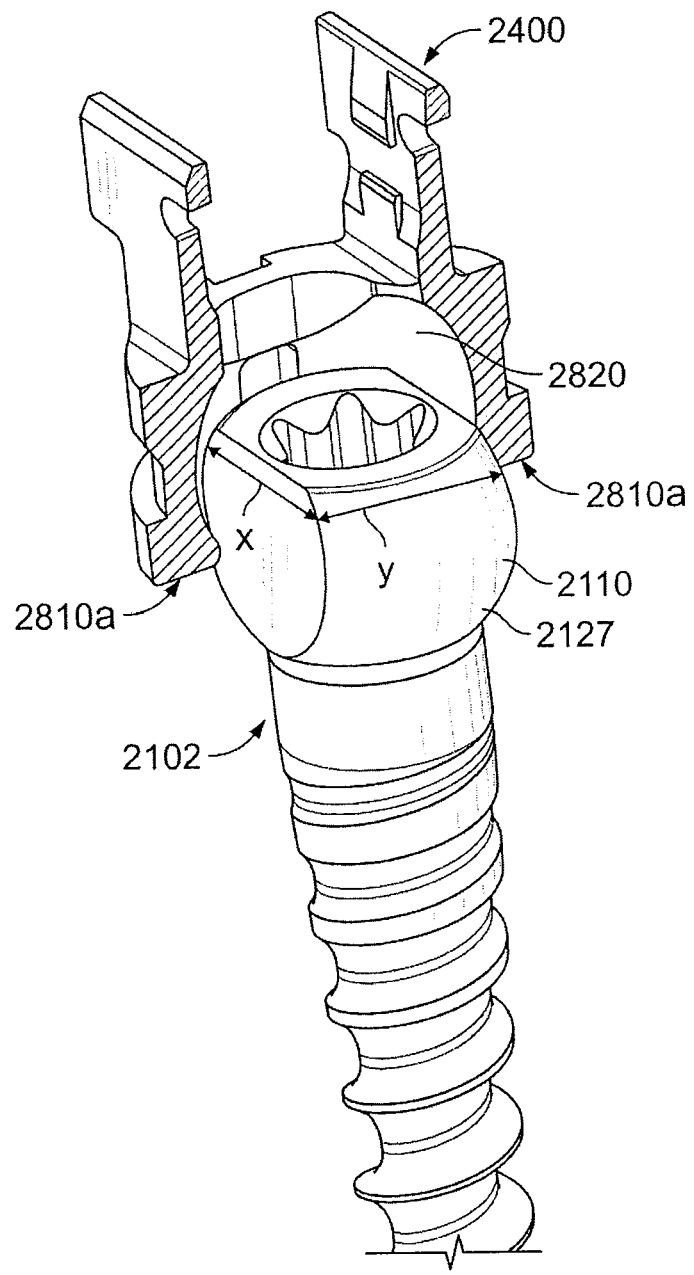
FIGS. 11A-11C depict insertion and retention of the bone anchor of FIG. 9 in the insert member of FIG. 10.
Figure 11B:
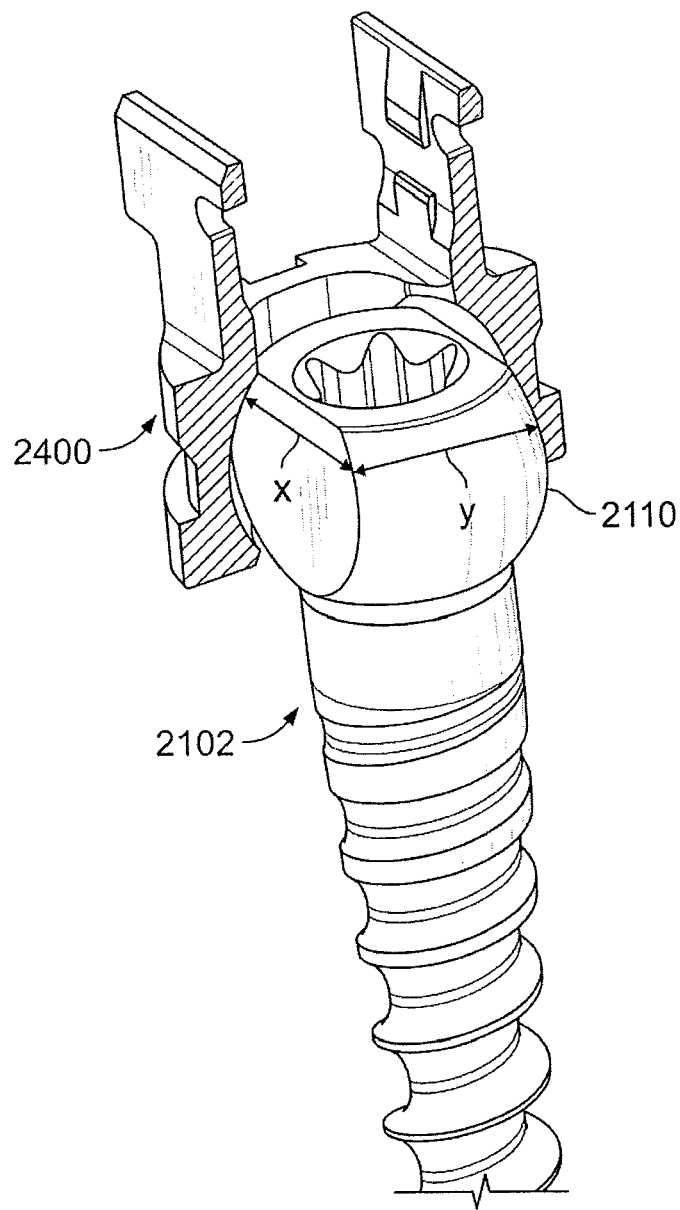
Figure 11C:
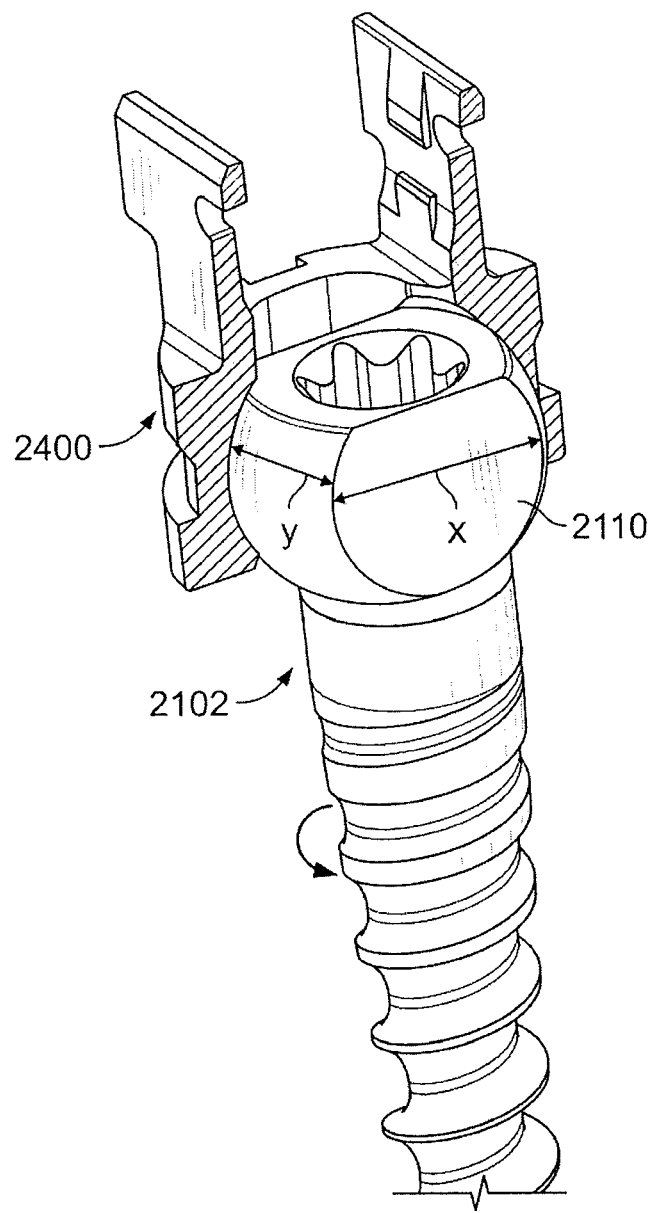
Figure 12A:
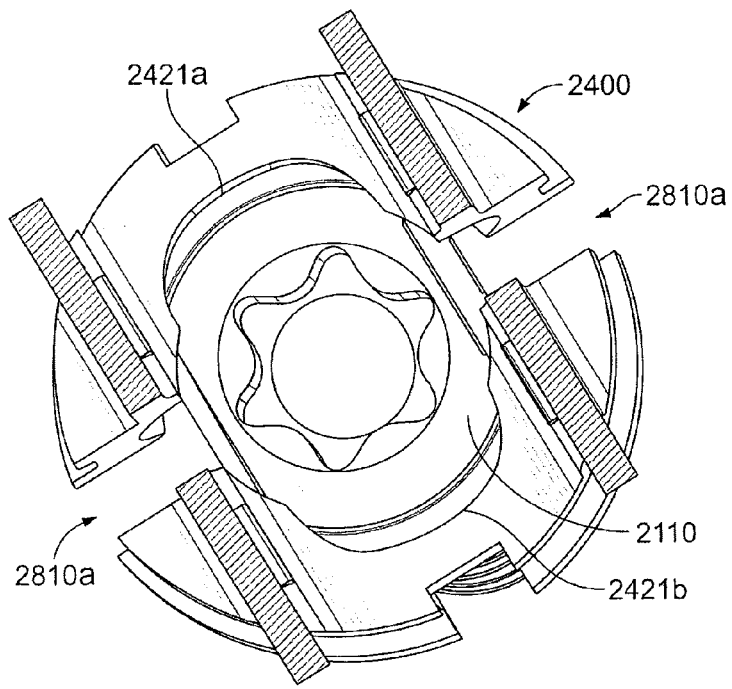
FIGS. 12A and 12B are top plan views of the insert member of FIGS. 10-11 demonstrating rotation of the bone anchor from FIG. 9 therein from an insertion position to a retention position.
Figure 12B:
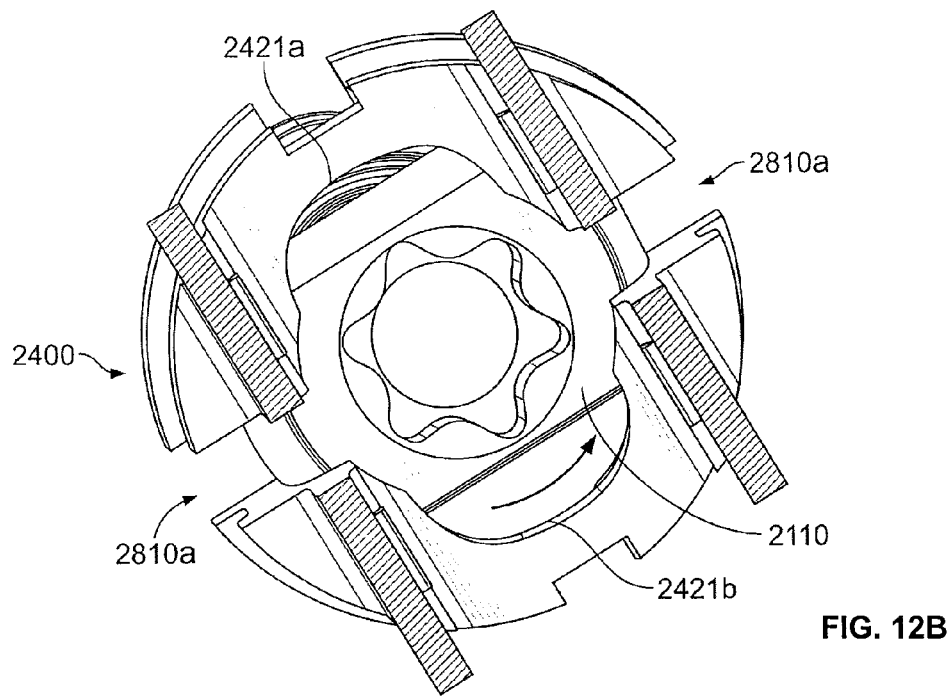

In use, the screw of FIGS. 9A-C may be inserted relatively easily into the insert member of FIGS. 10A-B when the first, larger, width of the screw head ("x") is aligned with the first, larger width ("a") of the opening 2860 in the lower end of the insert member 2400, but resists insertion from other orientations, such as when the first, larger width ("x") of the screw head is aligned with the second, narrower width ("b") of the opening in the insert member. Insertion and retention of the screw head into the insert member is demonstrated in FIGS. 11A-C, which depict a perspective view of the screw and a cut-away perspective view of the insert member 2400. Similar to other embodiments described herein, as the screw head is inserted into the cavity 2820 of the insert member 2400, as shown in FIG. 11A, major expansion gaps 2810a allow the insert member 2400 to flex, expanding the volume of the insert cavity 2820. Once the partially spherical surfaces 2127 of the head 2110 enter into the cavity, the flexible walls of the insert member flex back toward their original positions, closing around the screw head 2110 in a snap-lock arrangement. Although the insert member 2400 is at that point coupled to the screw head 2110, the insert member may still be removed with relative ease. For instance, the coupling assembly and screw head may be configured so that the coupling assembly may be removed by hand. In order to more securely hold the screw head, the insert member 2400 is rotated a predetermined amount (such as the approximately 90 degree rotation depicted) with respect to the screw 2102, so that the greater width of the insert member opening and the greater width of the screw head are out of phase, as shown in FIGS. 11c and 12B. The greater screw head width (x) is then aligned with the major expansion gaps 2810a.

Whereas the screw head 2110 contacts the annular wall portions of the insert member at points 2421a and 2421b in the insertion position (FIG. 12A), allowing the screw head to exit the insert member by expanding expansion gaps 2810a, in the retention position (FIG. 12B) the screw head 2110 does not contact wall portions 2421a and 2421b, and thus it is more difficult for forces applied to the screw or insert member to cause expansion of major expansion gaps 2810a. Thus, when the insert member is rotated to the screw retention position shown in FIGS. 11C and 12B, a greater amount of force must be applied to remove the screw head from the insert member cavity than when in the insertion position of FIGS. 11B and 12A. Advantageously, the screw head and insert member opening may be configured so that rotation of the insert member to this screw retention position ensures that the screw head will not escape the insert member cavity while the insert member is manipulated and placed under loads to engage and capture a spinal rod prior to locking of the assembly. Final locking of the screw relative to the insert member may be accomplished by axially shifting an outer member over the insert member 2400 in a manner similar to that described in connection with other embodiments herein.

The preceding descriptions of implants and instruments have been presented only to illustrate and describe the present methods and systems, and are not intended to be exhaustive or to limit the present systems and methods to any precise form disclosed. Many modifications and variations are possible in light of the above teachings.

The foregoing embodiments were chosen and described in order to illustrate principles of the systems and methods as well as some practical applications. The preceding description enables others skilled in the art to utilize the methods and systems in various embodiments and with various modifications as are suited to the particular use contemplated.

What is claimed is:
1. A multi-planar, polyaxial coupling assembly for securing an elongate member to a spine, the multi-planar, polyaxial coupling assembly comprising:

an anchor member having a head portion and a shank portion depending from the head portion with the anchor member having an axis along which the shank portion extends; and a coupling device having a cavity configured for snap-fit receipt of the anchor member head portion therein and to allow for pivotal and rotary adjustment of the anchor member so that the axis thereof can be oriented to extend in different directions and in different planes; wherein the coupling device has flexible wall portions that extend about the cavity, the anchor member head portion has a pair of opposite tapered and substantially flat side surface portions that taper toward each other up along the anchor member head portion so that an upper end portion of the anchor member head portion has a minimum width extending thereacross between the tapered side surface portions that is in clearance with the flexible wall portions for ease of insertion of anchor member head portion into the coupling device cavity for being snap-fit therein; and wherein the anchor member head portion is rotatable in the cavity to an anchor member retention position.

2. The multi-planar, polyaxial coupling assembly of claim 1 wherein the flexible wall portions have opposite, lower curved portions that curve toward each other, and the anchor member head portion has a lower end portion having a maximum width extending thereacross between the tapered side surface portions that is in interference with the opposite, lower curved portions of the coupling device flexible wall portions so that as the anchor member head portion is advanced upwardly into the cavity, the tapered side surface portions engage and cam the opposite, lower curved portions causing the flexible wall portions to shift away from each other until the lower end portion of the anchor member head portion clears the opposite, lower curved portions with the flexible wall portions shifting back toward each other so that the anchor member head portion is snap-fit in the coupling device cavity.

3. The multi-planar, polyaxial coupling assembly of claim 2 wherein the flexible wall portions have a pair of opposite major expansion gaps therebetween and a pair of opposite minor expansion gaps therebetween with the major expansion gaps being longer than the minor expansion gaps, and the anchor member head portion has opposite, curved surface portions and a maximum width extending thereacross between the opposite, curved surface portions that is larger than the maximum width across the lower end portion of the anchor member head portion between the tapered side surface portions thereof such that the anchor member head portion has to be received in the cavity in an anchor member insertion position with the curved surface portions facing the minor expansion gaps, and the anchor member head portion is rotatable in the cavity to the anchor member retention position so that the tapered side surface portions face the minor expansion gaps for keeping the anchor member head portion retained in the cavity against removal therefrom.

4. The multi-planar, polyaxial coupling assembly of claim 3 wherein in the insertion position the curved surface portions of the anchor member head portion contact portions of the flexible wall portions adjacent the minor expansion gaps, and in the retention position the tapered side surface portions of the anchor member head portion are spaced from the flexible wall portions adjacent the minor expansion gaps.

5. The multi-planar, polyaxial coupling assembly of claim 1 wherein the anchor member head portion has a wedge configuration.

6. The multi-planar, polyaxial coupling assembly of claim 1 wherein the anchor member head portion has opposite, generally spherical surface portions between the opposite tapered and substantially flat side surface portions.

7. The multi-planar, polyaxial coupling assembly of claim 1 wherein the coupling device has an insert member including the cavity, and an outer member having an inner space for receiving the insert member.

8. A method for securing an anchor member to a coupling device, the method comprising:
   aligning a head portion of the anchor member and a cavity of the coupling device in an insertion orientation relative to each other;
   advancing the aligned head portion into the cavity in the insertion orientation such that wall portions of the coupling device extending about the cavity and the head portion cooperate to allow the head portion to be removed from the cavity; and
   rotating the head portion in the coupling device cavity to a retention orientation in which the coupling device wall portions grip onto the head portion with a tighter gripping force over that exerted on the head portion in the insertion orientation to restrict removal of the head portion from the cavity.

9. The method of claim 8 wherein the head portion is rotated from the insertion orientation to the retention orientation by rotating the head portion by approximately ninety degrees.

10. The method of claim 8 wherein aligning the anchor member head portion and the coupling device cavity includes aligning a narrow width dimension of the anchor member head portion with a corresponding narrow width dimension of an opening to the cavity, and rotating the head portion to the retention orientation causes a larger width dimension of the anchor member head portion to be aligned with the narrow width dimension of the cavity opening.

11. The method of claim 8 including engaging flexible wall portions extending about the cavity of the coupling device at positions adjacent to opposite minor expansion gaps between the flexible wall portions and spaced circumferentially by approximately ninety degrees from longer, major expansion gaps between the flexible wall portions with the anchor member head portion in the cavity in the insertion orientation thereof, and rotating the anchor member head portion to the retention orientation in the cavity causes the anchor member head portion to be spaced from the flexible wall portions at the positions adjacent to the minor expansion gaps.

12. The method of claim 11 wherein engaging the flexible wall portions comprises engaging the flexible wall portions with a pair of opposite, curved surface portions of the anchor member head portion with the anchor member head portion in the cavity in the insertion orientation thereof, and rotating the anchor member head portion to the retention orientation causes a pair of opposite, substantially flat side surface portions of the anchor member head portion between the opposite, curved surface portions thereof to be spaced from the flexible wall portions at the positions adjacent to the minor expansion gaps.

13. The method of claim 8 including adjusting the anchor member with the head portion thereof received in the cavity with the anchor member being adjusted by allowing a shank portion of the anchor member to be oriented to extend in different directions and in different planes by either pivoting or rotating the anchor member, or both.

14. The method of claim 13 including locking the orientation of the anchor member shank portion relative to the coupling device by shifting an outer member of the coupling device to a predetermined position relative to an insert member of the coupling device with the cavity being formed in the insert member.

15. The method of claim 8 wherein advancing the aligned anchor member head portion into the cavity includes snap-fitting the anchor member head portion in the cavity.

16. The method of claim 15 wherein snap-fitting the anchor member head portion in the cavity includes camming lower portions of flexible wall portions of the coupling device extending about the cavity away from each other via engagement with a pair of opposite, tapered and substantially flat side surface portions of the anchor head member portion that taper toward each other up along the anchor member head portion.

* * * * *